US010076547B2

(12) United States Patent
Tani et al.

(10) Patent No.: US 10,076,547 B2
(45) Date of Patent: Sep. 18, 2018

(54) GENE-MODIFIED COXSACKIEVIRUS

(71) Applicant: KYUSHU UNIVERSITY NATIONAL UNIVERSITY CORPORATION, Fukuoka-shi, Fukuoka (JP)

(72) Inventors: Kenzaburo Tani, Fukuoka (JP); Shohei Miyamoto, Fukuoka (JP); Hiroyuki Inoue, Fukuoka (JP); Miyako Sagara, Fukuoka (JP)

(73) Assignees: SHIN NIHON SEIYAKU CO., LTD, Fukuoka-Shi (JP); KYUSHU UNIVERSITY NATIONAL UNIVERSITY CORPORATION, Fukuoka-Shi (JP)

( * ) Notice: Subject to any disclaimer, the term of this patent is extended or adjusted under 35 U.S.C. 154(b) by 34 days.

(21) Appl. No.: 14/785,222

(22) PCT Filed: Apr. 17, 2014

(86) PCT No.: PCT/JP2014/060988
§ 371 (c)(1),
(2) Date: Oct. 16, 2015

(87) PCT Pub. No.: WO2014/171526
PCT Pub. Date: Oct. 23, 2014

(65) Prior Publication Data

US 2016/0143969 A1 May 26, 2016

Related U.S. Application Data

(60) Provisional application No. 61/812,943, filed on Apr. 17, 2013.

(51) Int. Cl.

| | |
|---|---|
| ***A61K 35/768*** | (2015.01) |
| ***C12N 7/00*** | (2006.01) |
| ***A61K 35/76*** | (2015.01) |
| ***C12N 15/86*** | (2006.01) |

(52) U.S. Cl.
CPC ............ *A61K 35/768* (2013.01); *A61K 35/76* (2013.01); *C12N 7/00* (2013.01); *C12N 15/86* (2013.01); *C12N 2770/32032* (2013.01); *C12N 2770/32043* (2013.01); *C12N 2770/32321* (2013.01); *C12N 2770/32332* (2013.01); *C12N 2770/32343* (2013.01)

(58) Field of Classification Search
USPC ......... 435/6.6, 6.11, 91.31, 455, 6.16, 91.21, 435/91.1, 375, 377, 6.12, 6.13, 69.1, 435/320.1; 514/44; 536/23.1, 24.5
See application file for complete search history.

(56) References Cited

U.S. PATENT DOCUMENTS

| | | | |
|---|---|---|---|
| 2010/0047208 A1 | 2/2010 | Ke | |
| 2010/0111873 A1 | 5/2010 | Russell et al. | |

FOREIGN PATENT DOCUMENTS

| | | | | |
|---|---|---|---|---|
| JP | 2001-514509 | A | | 9/2001 |
| JP | 2007-527719 | A | | 10/2007 |
| JP | 2008-501349 | A | | 1/2008 |
| JP | 2008-501439 | A | | 1/2008 |
| JP | 2012-527465 | A | | 11/2012 |
| WO | 98-39426 | A | | 9/1998 |
| WO | WO 98/39426 | | * | 9/1998 |
| WO | 2005-087931 | A1 | | 9/2005 |
| WO | 2005/120635 | A1 | | 12/2005 |
| WO | 2008/103755 | A1 | | 8/2008 |
| WO | WO 2008/103755 | | * | 8/2008 |
| WO | 2010-135242 | A1 | | 11/2010 |
| WO | WO 2010/135242 | | * | 11/2010 |
| WO | 2012/094836 | A1 | | 7/2012 |
| WO | 2012/129385 | A1 | | 9/2012 |

OTHER PUBLICATIONS

Kelly et al, Nature Medicine, vol. 14, No. 11, pp. 1278-1283 (2008).
Dephino et al WO 2010/135242.*
Liu, Zhewei et al., "Structural and Functional Analysis of the 5' Untranslated Region of Coxsackievirus B3 RNA: In Vivo Translational and Infectivity Studies of Full-Length Mutants", Virology, vol. 265, 1999, pp. 206-217.
Gauntt, Charles J., et al., "Coxsackievirus B3 clinical isolates and murine myocarditis", Virus Research, vol. 41, 1996, pp. 89-99.
Henke, Andreas et al., "Recombinant coxsackievirus vectors for prevention and therapy of virus-induced heart disease", International Journal of Medical Mircobiology, 2008, pp. 127-134.
Miyamoto, Shohei et al., "Coxsackievirus B3 Is an Oncolytic Virus with Immunostimulatory Properties That Is Active against Lung Adenocarcinoma", Cancer Research, vol. 72, No. 10, 2012, pp. 2609-2621.
Kelly, Elizabeth J., et al., "Engineering microRNA responsiveness to decrease virus pathogenicity", Nature Medicine, vol. 14 No. 11, Nov. 2008, pp. 1278-1283.
Search Report dated Jul. 22, 2014, issued in counterpart international Application No. PCT/JP2014/060988 (4 pages).
International Preliminary Report on Patentability (PCT/IPEA/416) issued in counterpart International Application No. PCT/JP2014/060988 dated Oct. 22, 2015, with English translation, PCT/IB/338, PCT/IPEA/409. (24 pages).
Vuorinen, Tytti et al., "Coxsackievirus B3-induced acute pancreatitis: analysis of histopathological and viral parameters in a mouse model", The British Journal of Experimental Pathology, vol. 70, 1989, pp. 395-403.
Gebhard. John R. et al., "Coxsackievirus B3-Induced Myocarditis", American Journal of Pathology, vol. 153, No. 2, Aug. 1998, pp. 417-428.

(Continued)

*Primary Examiner* — Jane Zara
(74) *Attorney, Agent, or Firm* — Westerman, Hattori, Daniels & Adrian, LLP

(57) ABSTRACT

A modified coxsackievirus showing improved safety and/or aggressiveness to be used for oncolytic virotherapy is provided. A modified coxsackievirus showing tissue-specific suppression of proliferation and comprising a mutated genome consisting of the genome of coxsackievirus B3 wild-type (CVB3-WT) inserted with at least one polynucleotide consisting of a target sequence of tissue-specific microRNA (miRNA) is provided. The mutated genome is preferably further inserted with the region encoding GM-CSF in an expressible form.

17 Claims, 18 Drawing Sheets

Specification includes a Sequence Listing.

(56) References Cited

OTHER PUBLICATIONS

He, Bin et al., “Role of miR-1 and miR-133a in myocardial ischemic postconditioning”, Journal of Biomedical Science, 2011, pp. 1-10.
Szafranska, AE et al., “MicroRNA expression alterations are linked to tumorigenesis and non-neoplastic processes in pancreatic ductal adenocarcinoma”, Oncogene, Nature Publishing Group, 2007, vol. 26, pp. 4442-4452.
Office Action dated Feb. 6, 2018, issued in counterpart Japanese Application No. 2015-512529, with English machine translation. (7 pages).

* cited by examiner

[Fig.1]
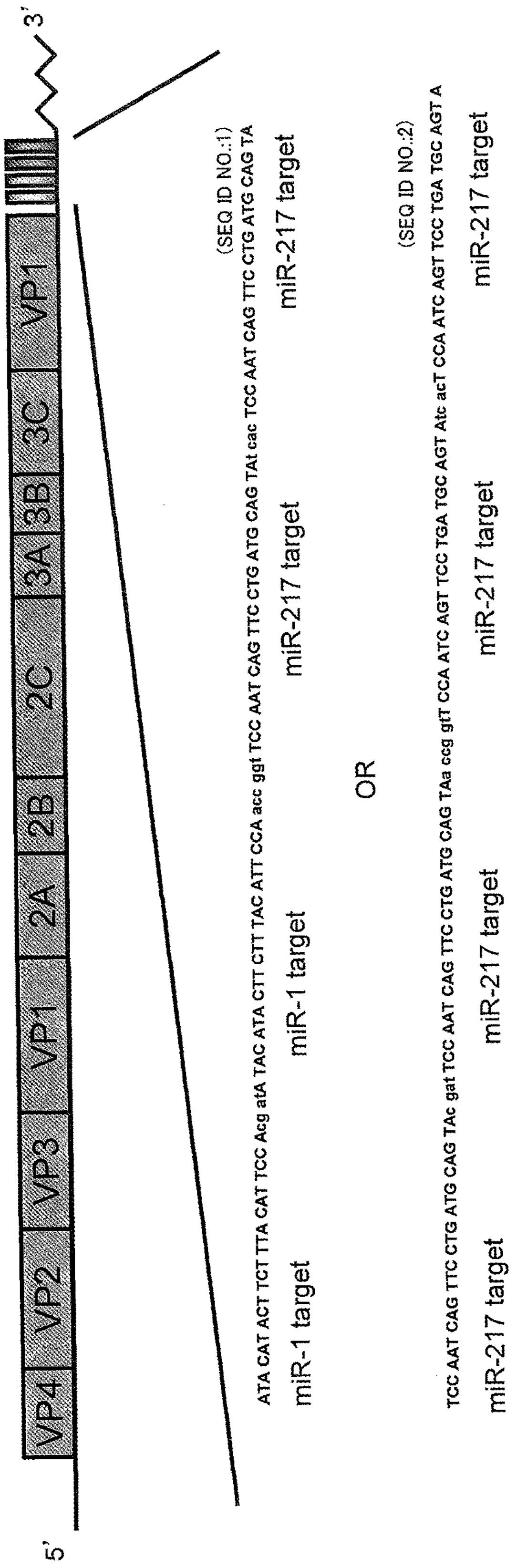

[Fig.2]
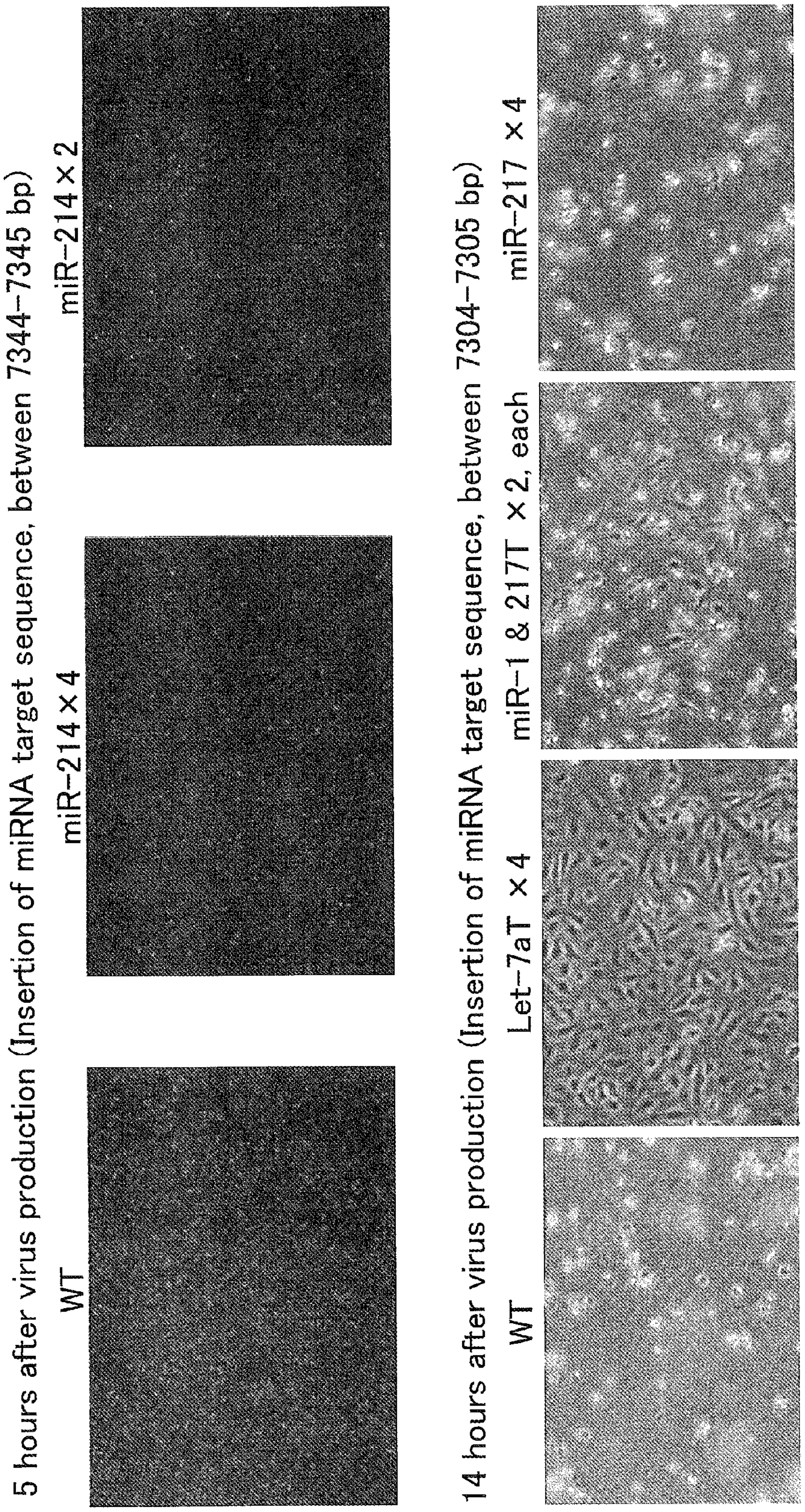

[Fig.3]
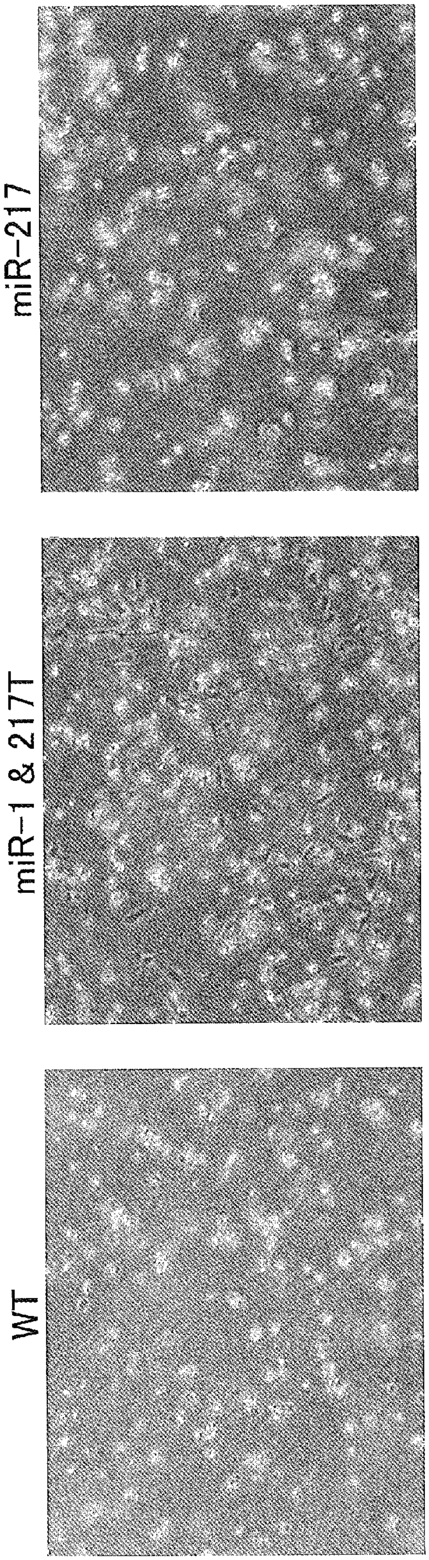
WT
miR-1 & 217T
miR-217

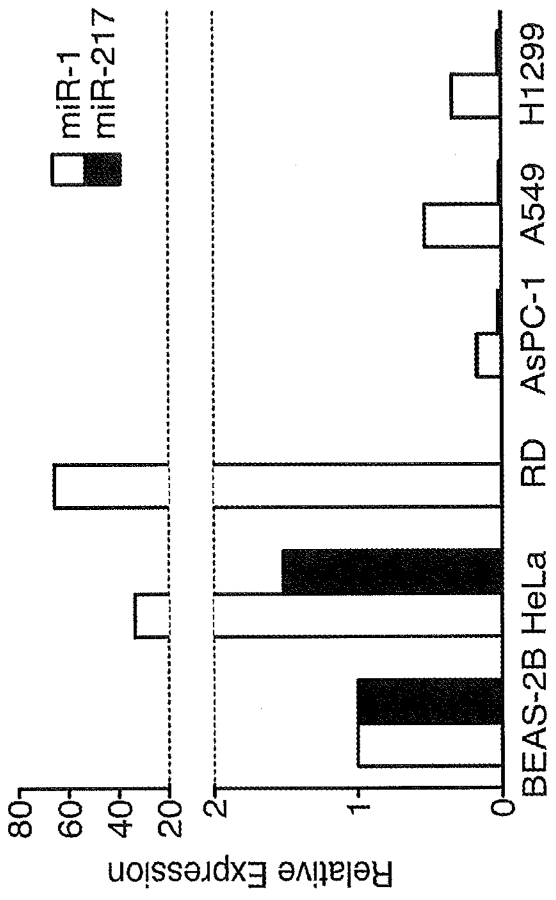
[Fig.4]

[Fig.5]
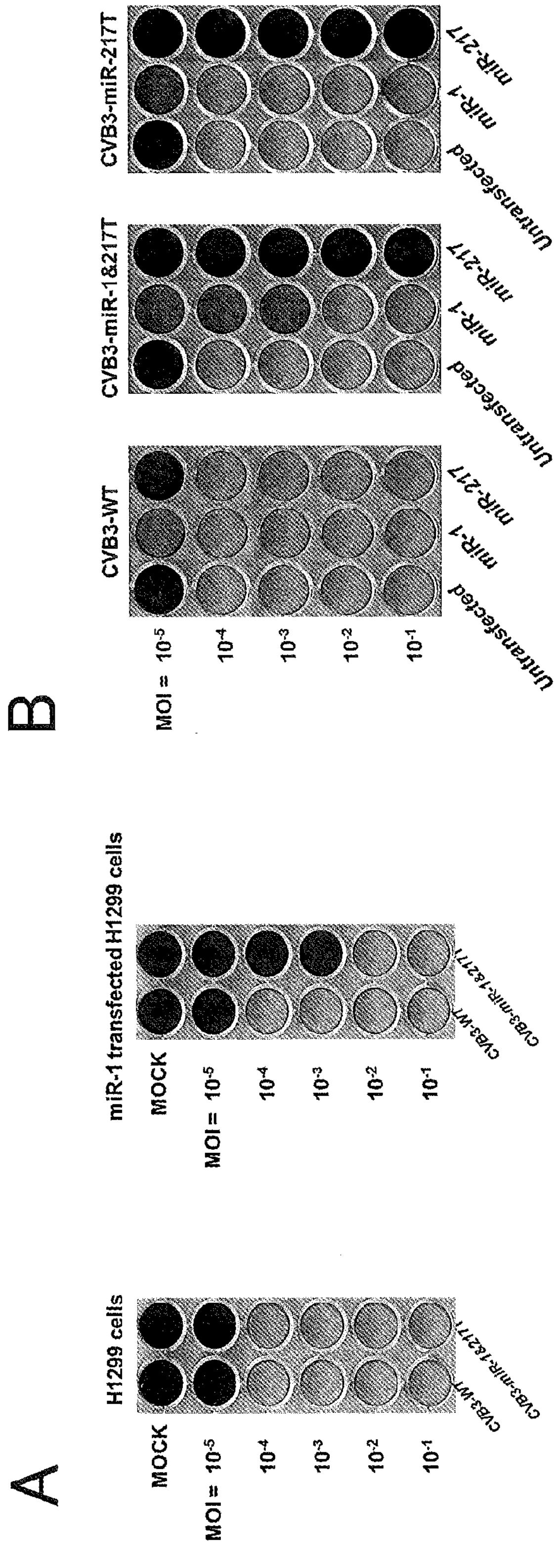

[Fig.6]
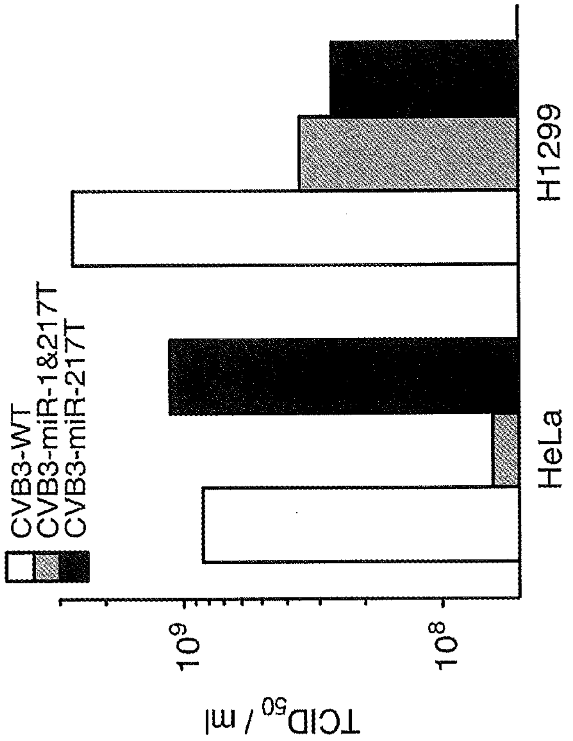

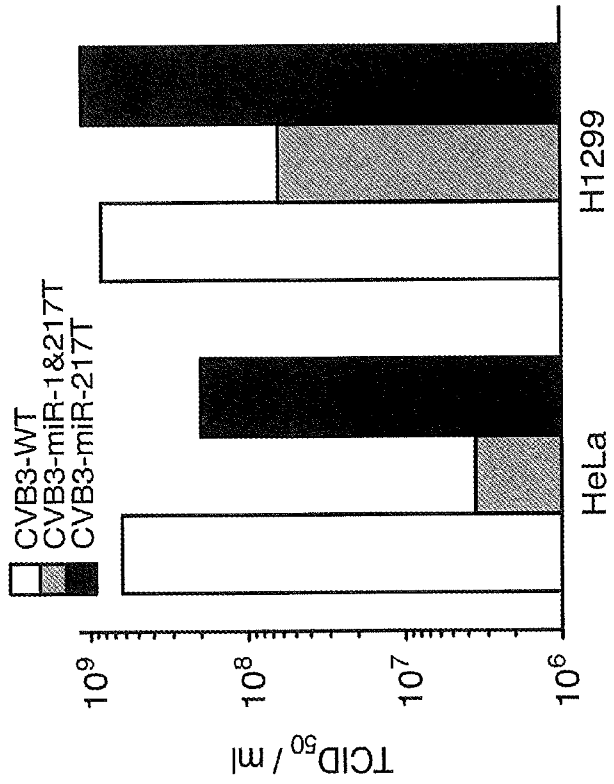
[Fig.7]

[Fig.8]
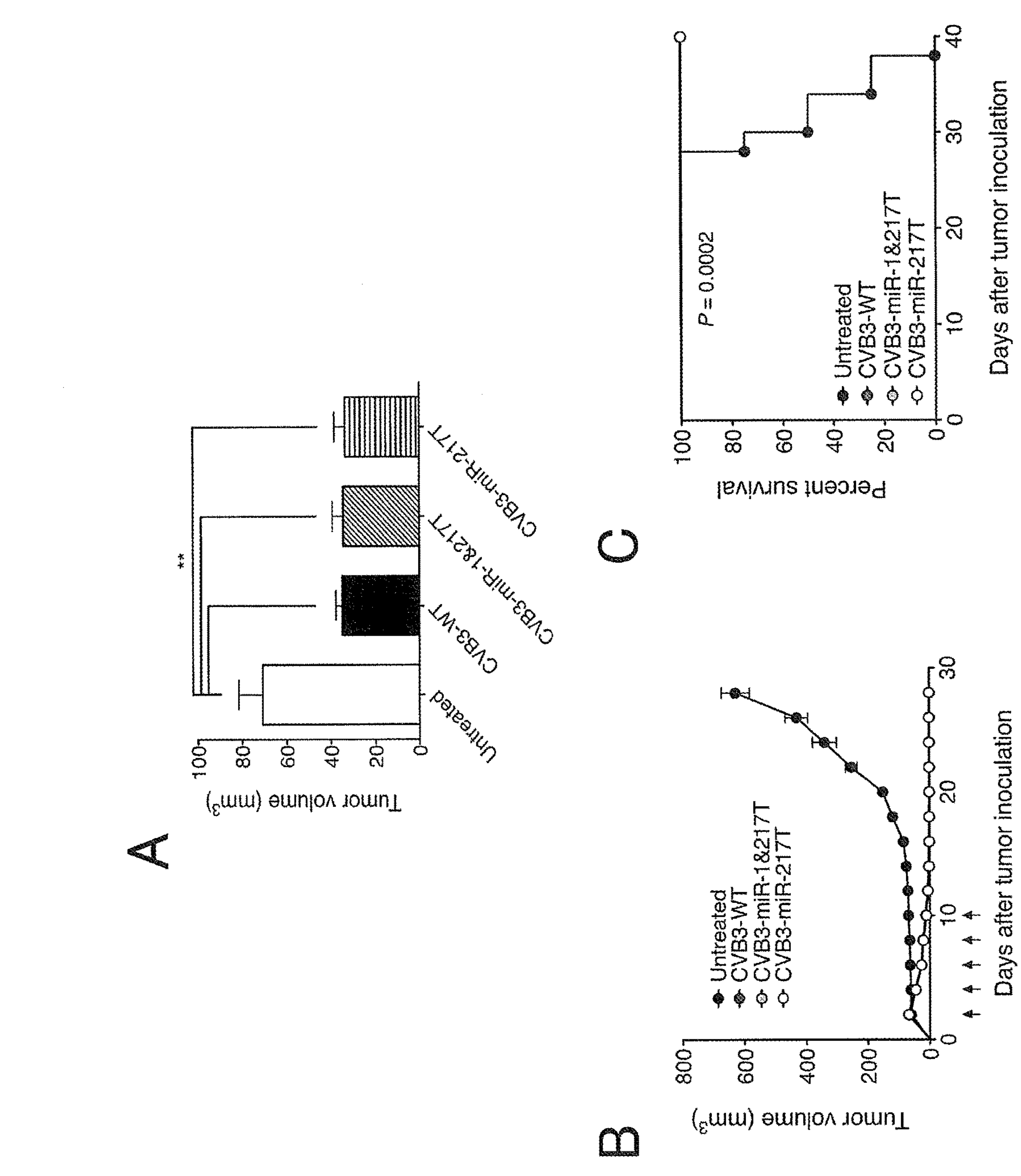

[Fig.9]
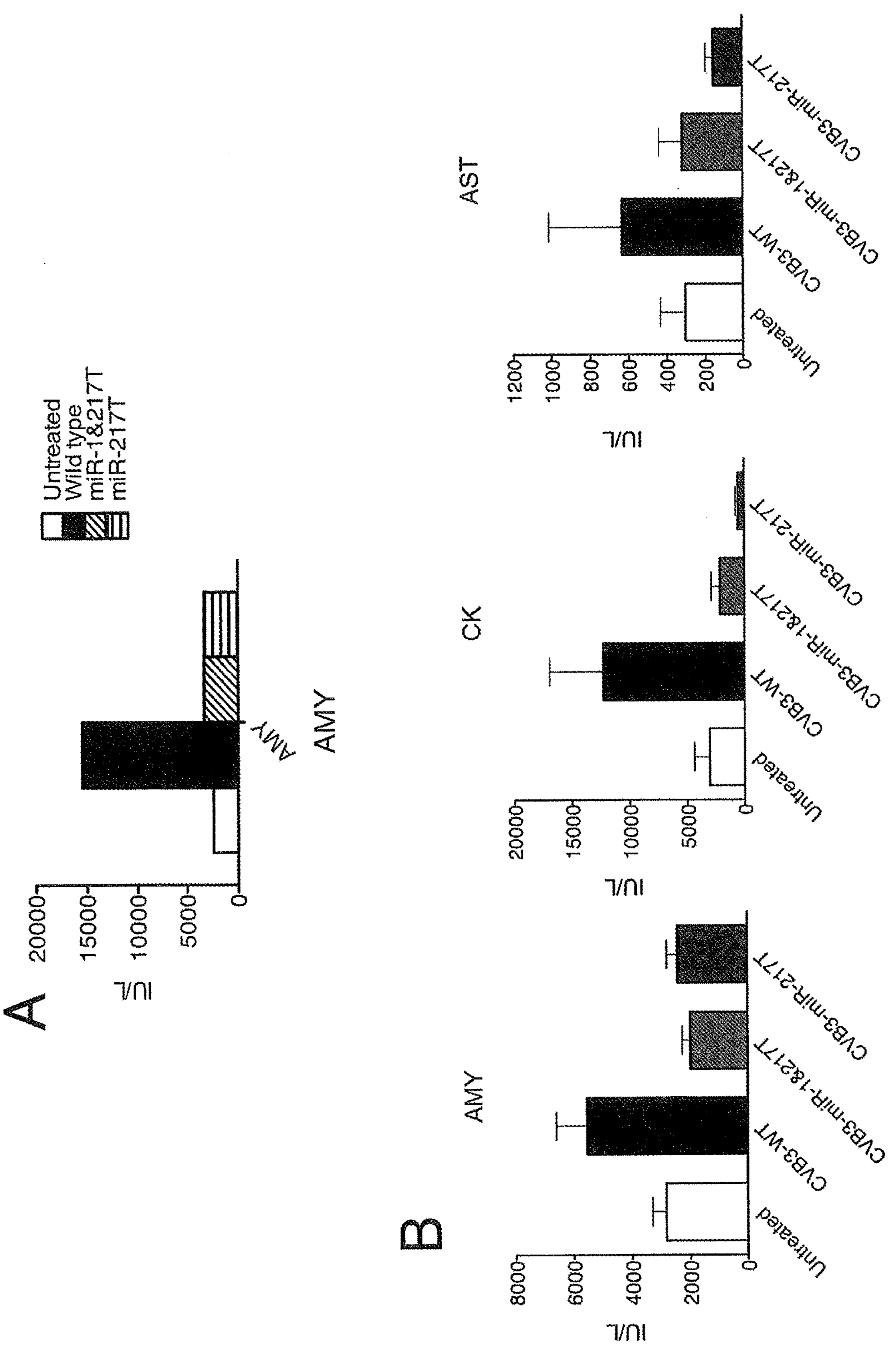

[Fig.10]
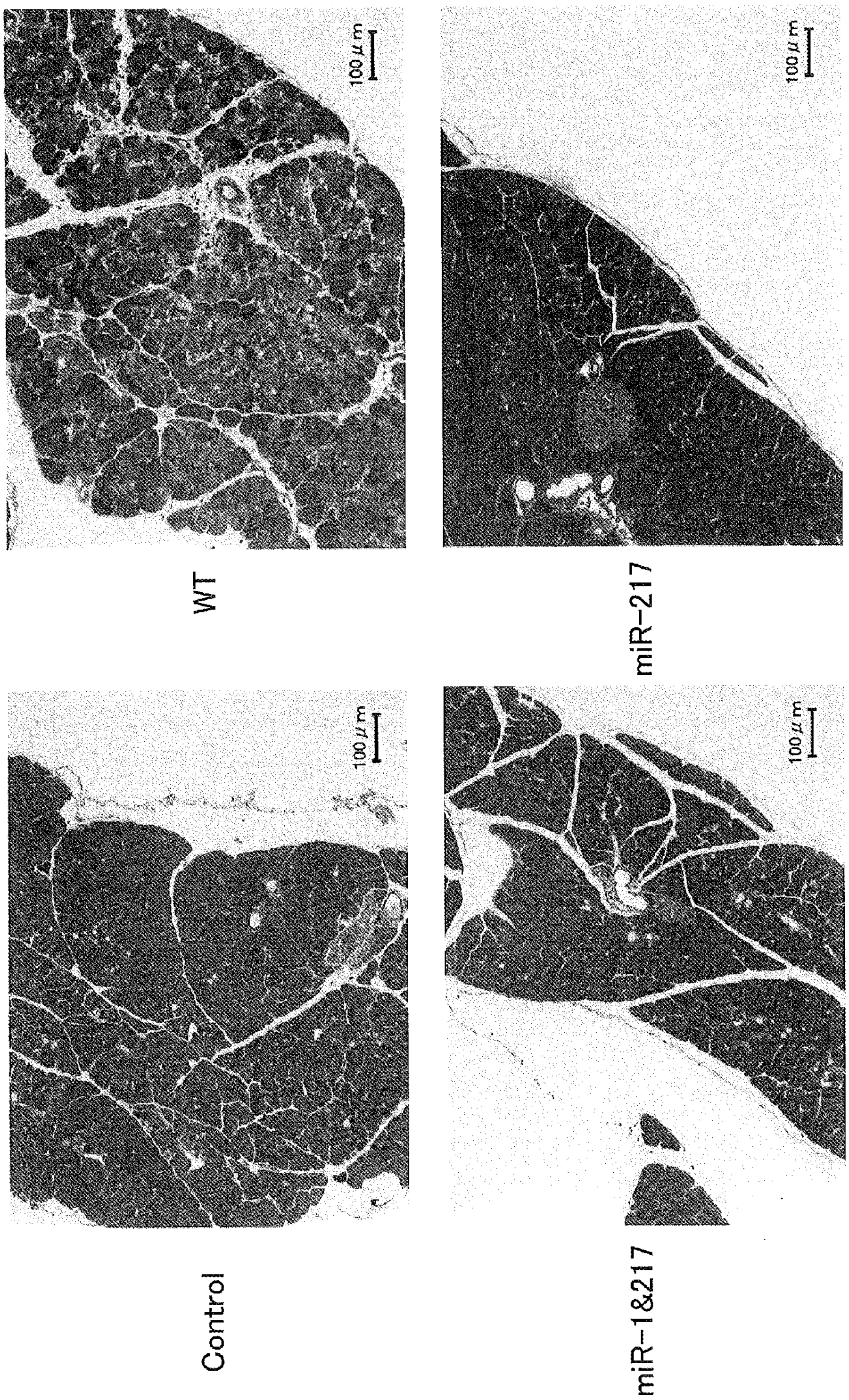

[Fig.11]
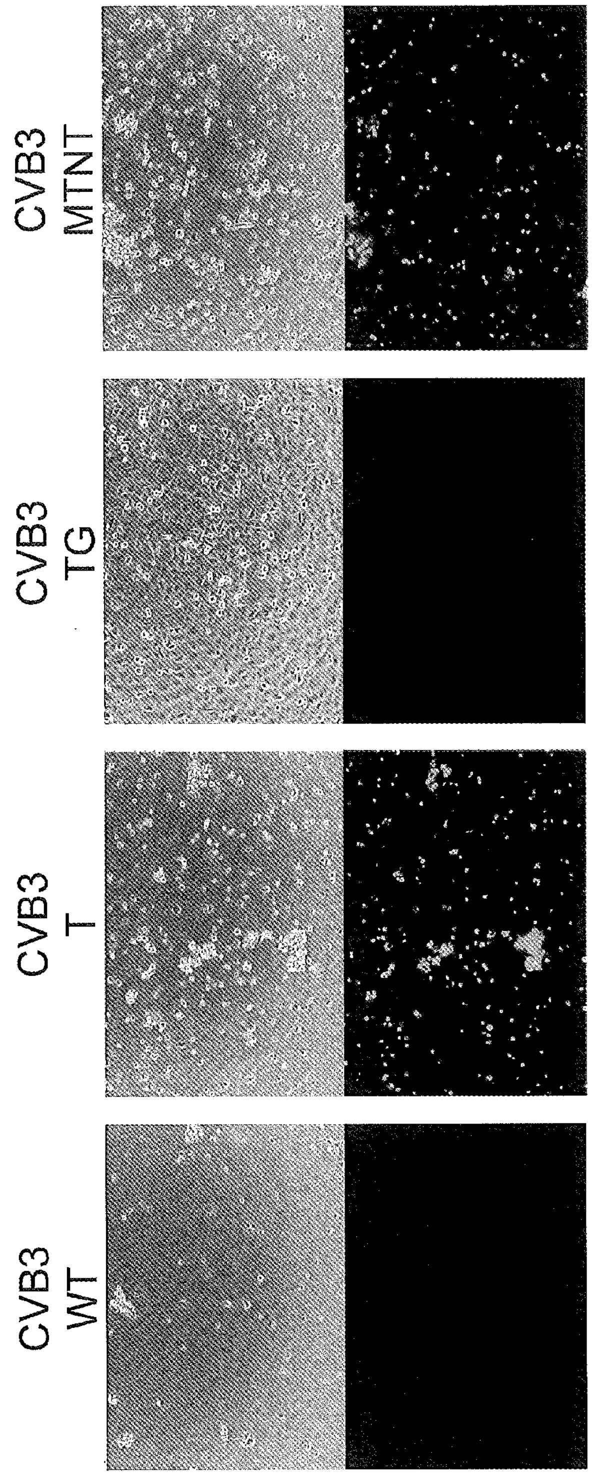

[Fig.12]
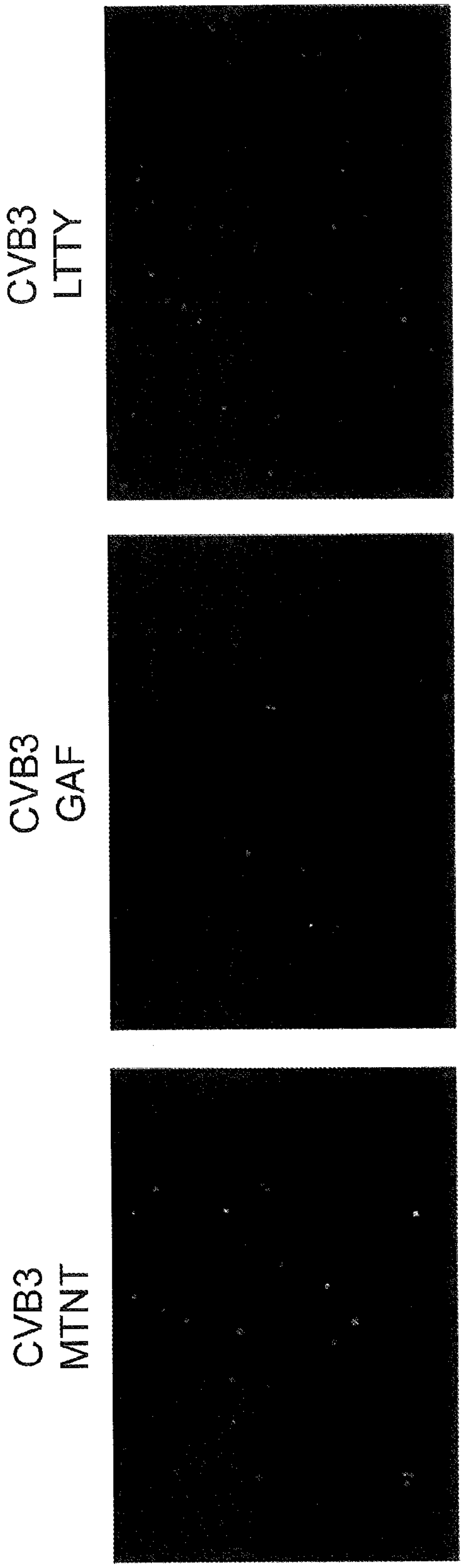

[Fig.13]
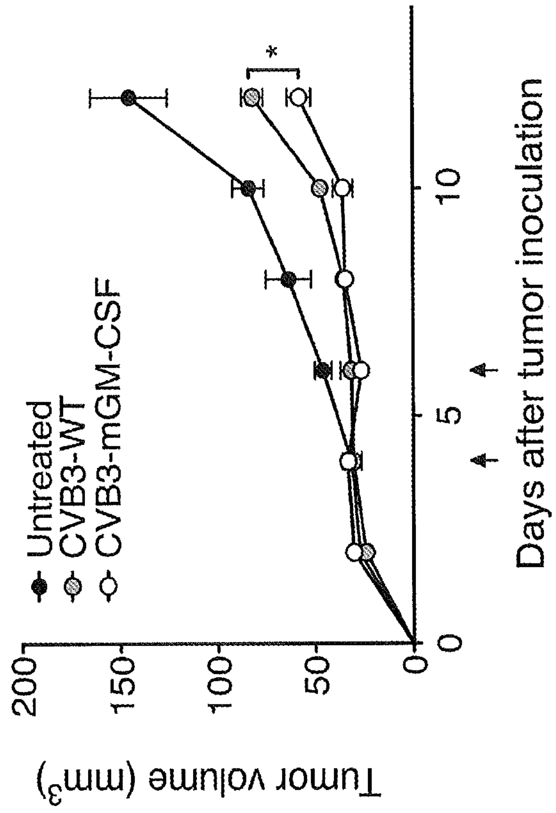

[Fig.14]

- CVB3-GM-CSF-2A (SEQ ID NO.:3)
- atgGCAGCTCAAATCGATtggctgcagaatttacttttcctgggcattgtggtctacagcctctcagcacccacccgctcacccatca
ctgtcacccggccttggaagcatgtagaggccatcaaagaagccctgaacctcctggatgacatgcctgtcacgttgaatgaagaggtagaag
tcgtctctaacgagttctccttcaagaagctaacatgtgtgcagacccgcctgaagatattcgagcagggtctacggggcaatttcaccaaact
caagggcgccttgaacatgacagccagctactaccagacatactgcccccaactccggaaacggactgtgaaacacaagttaccacctat
gcggatttcatagacagccttaaaacctttctgactgatatcccctttgaatgcaaaaaaccaggccaaaaaGAGGGCAGAGGAAGT
CTTCTAACATGCGGTGACGTGGAGGAGAATCCCGGCCCT

- CVB3-GM-CSF-LTTY (SEQ ID NO.:4)
- atgGCAGCTCAAATCGATtggctgcagaatttacttttcctgggcattgtggtctacagcctctcagcacccacccgctcacccatca
ctgtcacccggccttggaagcatgtagaggccatcaaagaagccctgaacctcctggatgacatgcctgtcacgttgaatgaagaggtagaag
tcgtctctaacgagttctccttcaagaagctaacatgtgtgcagacccgcctgaagatattcgagcagggtctacggggcaatttcaccaaact
caagggcgccttgaacatgacagccagctactaccagacatactgcccccaactccggaaacggactgtgaaacacaagttaccacctat
gcggatttcatagacagccttaaaacctttctgactgatatcccctttgaatgcaaaaaaccaggccaaaaaCCCTGCAGGGATCTT
ACAACGTAC

- CVB3-GM-CSF-AVFQ (SEQ ID NO.:5)
- atgGGGGCCGGAGAGGCCtggctgcagaatttacttttcctgggcattgtggtctacagcctctcagcacccacccgctcacccatc
actgtcacccggccttggaagcatgtagaggccatcaaagaagccctgaacctcctggatgacatgcctgtcacgttgaatgaagaggtagaa
gtcgtctctaacgagttctccttcaagaagctaacatgtgtgcagacccgcctgaagatattcgagcagggtctacggggcaatttcaccaaac
tcaagggcgccttgaacatgacagccagctactaccagacatactgcccccaactccggaaacggactgtgaaacacaagttaccaccta
tgcggatttcatagacagccttaaaacctttctgactgatatcccctttgaatgcaaaaaaccaggccaaaaaGCCAGAGGGGCCTG
CTGCGAGTTTGCAggacttagacaagcagtttttcaa

SEQUENCE LISTING

```
<160> NUMBER OF SEQ ID NOS: 44

<210> SEQ ID NO 1
<211> LENGTH: 104
<212> TYPE: DNA
<213> ORGANISM: Artificial Sequence
<220> FEATURE:
<223> OTHER INFORMATION: miR-1 & 217T (x2)

<400> SEQUENCE: 1

atacatactt ctttacattc cacgatatac atacttcttt acattccaac cggttccaat     60

cagttcctga tgcagtatca ctccaatcag ttcctgatgc agta                     104


<210> SEQ ID NO 2
<211> LENGTH: 106
<212> TYPE: DNA
<213> ORGANISM: Artificial Sequence
<220> FEATURE:
<223> OTHER INFORMATION: miR-217T (x4)

<400> SEQUENCE: 2

tccaatcagt tcctgatgca gtacgattcc aatcagttcc tgatgcagta accggttcca     60

atcagttcct gatgcagtat cactccaatc agttcctgat gcagta                   106


<210> SEQ ID NO 3
<211> LENGTH: 492
<212> TYPE: DNA
<213> ORGANISM: Artificial Sequence
<220> FEATURE:
<223> OTHER INFORMATION: CVB3-GM-CSF-2A

<400> SEQUENCE: 3

atggcagctc aaatcgattg gctgcagaat ttacttttcc tgggcattgt ggtctacagc     60

ctctcagcac ccacccgctc acccatcact gtcacccggc cttggaagca tgtagaggcc    120

atcaaagaag ccctgaacct cctggatgac atgcctgtca cgttgaatga agaggtagaa    180

gtcgtctcta acgagttctc cttcaagaag ctaacatgtg tgcagacccg cctgaagata    240

ttcgagcagg gtctacgggg caatttcacc aaactcaagg gcgccttgaa catgacagcc    300

agctactacc agacatactg ccccccaact ccggaaacgg actgtgaaac acaagttacc    360

acctatgcgg atttcataga cagccttaaa acctttctga ctgatatccc ctttgaatgc    420

aaaaaaccag gccaaaaaga gggcagagga agtcttctaa catgcggtga cgtggaggag    480

aatcccggcc ct                                                        492


<210> SEQ ID NO 4
```

-continued

```
<211> LENGTH: 462
<212> TYPE: DNA
<213> ORGANISM: Artificial Sequence
<220> FEATURE:
<223> OTHER INFORMATION: CVB3-GM-CSF-LTTY

<400> SEQUENCE: 4

atggcagctc aaatcgattg gctgcagaat ttacttttcc tgggcattgt ggtctacagc     60

ctctcagcac ccacccgctc acccatcact gtcacccggc cttggaagca tgtagaggcc    120

atcaaagaag ccctgaacct cctggatgac atgcctgtca cgttgaatga agaggtagaa    180

gtcgtctcta acgagttctc cttcaagaag ctaacatgtg tgcagacccg cctgaagata    240

ttcgagcagg gtctacgggg caatttcacc aaactcaagg gcgccttgaa catgacagcc    300

agctactacc agacatactg ccccccaact ccggaaacgg actgtgaaac acaagttacc    360

acctatgcgg atttcataga cagccttaaa acctttctga ctgatatccc ctttgaatgc    420

aaaaaaccag gccaaaaacc ctgcagggat cttacaacgt ac                       462


<210> SEQ ID NO 5
<211> LENGTH: 489
<212> TYPE: DNA
<213> ORGANISM: Artificial Sequence
<220> FEATURE:
<223> OTHER INFORMATION: CVB3-GM-CSF-AVFQ

<400> SEQUENCE: 5

atgggggccg gagaggcctg gctgcagaat ttacttttcc tgggcattgt ggtctacagc     60

ctctcagcac ccacccgctc acccatcact gtcacccggc cttggaagca tgtagaggcc    120

atcaaagaag ccctgaacct cctggatgac atgcctgtca cgttgaatga agaggtagaa    180

gtcgtctcta acgagttctc cttcaagaag ctaacatgtg tgcagacccg cctgaagata    240

ttcgagcagg gtctacgggg caatttcacc aaactcaagg gcgccttgaa catgacagcc    300

agctactacc agacatactg ccccccaact ccggaaacgg actgtgaaac acaagttacc    360

acctatgcgg atttcataga cagccttaaa acctttctga ctgatatccc ctttgaatgc    420

aaaaaaccag gccaaaaagc cagaggggcc tgctgcgagt ttgcaggact tagacaagca    480

gtttttcaa                                                            489


<210> SEQ ID NO 6
<211> LENGTH: 20
<212> TYPE: DNA
<213> ORGANISM: Artificial Sequence
<220> FEATURE:
<223> OTHER INFORMATION: CVB3-miR-Forward primer

<400> SEQUENCE: 6

caggtctttg aggggaacaa                                                 20


<210> SEQ ID NO 7
<211> LENGTH: 20
<212> TYPE: DNA
<213> ORGANISM: Artificial Sequence
<220> FEATURE:
<223> OTHER INFORMATION: CVB3-miR-Reverse primer

<400> SEQUENCE: 7

attaatgcag ctggcacgac                                                 20


<210> SEQ ID NO 8
<211> LENGTH: 129
```

-continued

```
<212> TYPE: DNA
<213> ORGANISM: Artificial Sequence
<220> FEATURE:
<223> OTHER INFORMATION: miR-1&217T Forward primer

<400> SEQUENCE: 8

ttaatacata cttctttaca ttccacgata tacatacttc tttacattcc aaccggttcc     60

aatcagttcc tgatgcagta tcactccaat cagttcctga tgcagtagag acaatttgaa    120

ataatttag                                                            129


<210> SEQ ID NO 9
<211> LENGTH: 129
<212> TYPE: DNA
<213> ORGANISM: Artificial Sequence
<220> FEATURE:
<223> OTHER INFORMATION: miR-1&217T Reverse primer

<400> SEQUENCE: 9

ctctactgca tcaggaactg attggagtga tactgcatca ggaactgatt ggaaccggtt     60

ggaatgtaaa gaagtatgta tatcgtggaa tgtaaagaag tatgtattaa tctaaaagga    120

gtccaacca                                                            129


<210> SEQ ID NO 10
<211> LENGTH: 131
<212> TYPE: DNA
<213> ORGANISM: Artificial Sequence
<220> FEATURE:
<223> OTHER INFORMATION: miR-217T Forward primer

<400> SEQUENCE: 10

ttatccaatc agttcctgat gcagtacgat tccaatcagt tcctgatgca gtaaccggtt     60

ccaatcagtt cctgatgcag tatcactcca atcagttcct gatgcagtag agacaatttg    120

aaataattta g                                                         131


<210> SEQ ID NO 11
<211> LENGTH: 20
<212> TYPE: DNA
<213> ORGANISM: Artificial Sequence
<220> FEATURE:
<223> OTHER INFORMATION: CVB3-Forward primer

<400> SEQUENCE: 11

gcactcactg ctgctgagac                                                 20


<210> SEQ ID NO 12
<211> LENGTH: 20
<212> TYPE: DNA
<213> ORGANISM: Artificial Sequence
<220> FEATURE:
<223> OTHER INFORMATION: CVB3-Reverse primer

<400> SEQUENCE: 12

aggtcatcgt ggttcctcac                                                 20


<210> SEQ ID NO 13
<211> LENGTH: 20
<212> TYPE: DNA
<213> ORGANISM: Artificial Sequence
<220> FEATURE:
<223> OTHER INFORMATION: EGFP-Forward primer

<400> SEQUENCE: 13
```

-continued gtgagcaagg gcgaggagct 20

<210> SEQ ID NO 14
<211> LENGTH: 20
<212> TYPE: DNA
<213> ORGANISM: Artificial Sequence
<220> FEATURE:
<223> OTHER INFORMATION: EGFP-Forward primer

<400> SEQUENCE: 14
cttgtacagc tcgtccatgc 20

<210> SEQ ID NO 15
<211> LENGTH: 63
<212> TYPE: DNA
<213> ORGANISM: Artificial Sequence
<220> FEATURE:
<223> OTHER INFORMATION: CVB3-G-EGFP-T-Fw primer

<400> SEQUENCE: 15
atcactctcg gcatggacga gctgtacaag acgggcgcat ttggacaaca atcaggggca 60
gtg 63

<210> SEQ ID NO 16
<211> LENGTH: 63
<212> TYPE: DNA
<213> ORGANISM: Artificial Sequence
<220> FEATURE:
<223> OTHER INFORMATION: CVB3-G-EGFP-T-Rev primer

<400> SEQUENCE: 16
cccggtgaac agctcctcgc ccttgctcac gcccgtattt gtcattgtag tgatgctttg 60
cct 63

<210> SEQ ID NO 17
<211> LENGTH: 66
<212> TYPE: DNA
<213> ORGANISM: Artificial Sequence
<220> FEATURE:
<223> OTHER INFORMATION: CVB3-TG-EGFP-TG-Fw primer

<400> SEQUENCE: 17
atcactctcg gcatggacga gctgtacaag acgggcggcg catttggaca acaatcaggg 60
gcagtg 66

<210> SEQ ID NO 18
<211> LENGTH: 66
<212> TYPE: DNA
<213> ORGANISM: Artificial Sequence
<220> FEATURE:
<223> OTHER INFORMATION: CVB3-TG-EGFP-TG-Rev primer

<400> SEQUENCE: 18
cccggtgaac agctcctcgc ccttgctcac gcccgtcgta tttgtcattg tagtgatgct 60
ttgcct 66

<210> SEQ ID NO 19
<211> LENGTH: 72
<212> TYPE: DNA
<213> ORGANISM: Artificial Sequence
<220> FEATURE:
<223> OTHER INFORMATION: GAFGQQ-EGFP-MTNT-Fw primer

<400> SEQUENCE: 19
atcactctcg gcatggacga gctgtacaag atgacaaata cgggcgcatt tggacaacaa 60
tcaggggcag tg 72

<210> SEQ ID NO 20
<211> LENGTH: 78
<212> TYPE: DNA
<213> ORGANISM: Artificial Sequence
<220> FEATURE:
<223> OTHER INFORMATION: GAFGQQ-EGFP-MTNT-Rev primer

<400> SEQUENCE: 20
cccggtgaac agctcctcgc ccttgctcac ttgttgtcca aatgcgcccg tatttgtcat 60
tgtagtgatg ctttgcct 78

<210> SEQ ID NO 21
<211> LENGTH: 20
<212> TYPE: DNA
<213> ORGANISM: Artificial Sequence
<220> FEATURE:
<223> OTHER INFORMATION: CVB3-Forward primer

<400> SEQUENCE: 21
gcactcactg ctgctgagac 20

<210> SEQ ID NO 22
<211> LENGTH: 20
<212> TYPE: DNA
<213> ORGANISM: Artificial Sequence
<220> FEATURE:
<223> OTHER INFORMATION: CVB3-Reverse primer

<400> SEQUENCE: 22
aggtcatcgt ggttcctcac 20

<210> SEQ ID NO 23
<211> LENGTH: 34
<212> TYPE: DNA
<213> ORGANISM: Artificial Sequence
<220> FEATURE:
<223> OTHER INFORMATION: LTTY substitution Forward

<400> SEQUENCE: 23
cttacaacgt acggcgcatt tggacaacaa tcag 34

<210> SEQ ID NO 24
<211> LENGTH: 20
<212> TYPE: DNA
<213> ORGANISM: Artificial Sequence
<220> FEATURE:
<223> OTHER INFORMATION: GQQ deletion Forward primer

<400> SEQUENCE: 24
aaatgcgccc gtatttgtca 20

<210> SEQ ID NO 25
<211> LENGTH: 20
<212> TYPE: DNA
<213> ORGANISM: Artificial Sequence
<220> FEATURE:
<223> OTHER INFORMATION: CVB3-Forward primer

<400> SEQUENCE: 25 tatacccct cccccaactg 20

-continued

<210> SEQ ID NO 26
<211> LENGTH: 20
<212> TYPE: DNA
<213> ORGANISM: Artificial Sequence
<220> FEATURE:
<223> OTHER INFORMATION: CVB3-Reverse primer

<400> SEQUENCE: 26
agcaagcatc cttggtggaa 20

<210> SEQ ID NO 27
<211> LENGTH: 72
<212> TYPE: DNA
<213> ORGANISM: Artificial Sequence
<220> FEATURE:
<223> OTHER INFORMATION: Cla&Sbf-Forward primer

<400> SEQUENCE: 27
atggcagctc aaatcgattt tggggggccc tgcagggagg ctttgtttca aggagctcaa 60
gtatcaacgc aa 72

<210> SEQ ID NO 28
<211> LENGTH: 72
<212> TYPE: DNA
<213> ORGANISM: Artificial Sequence
<220> FEATURE:
<223> OTHER INFORMATION: Cla&Sbf-Reverse primer

<400> SEQUENCE: 28
tccttgaaac aaagcctccc tgcagggccc cccaaaatcg atttgagctg ccattttgct 60
gtattcaact ta 72

<210> SEQ ID NO 29
<211> LENGTH: 35
<212> TYPE: DNA
<213> ORGANISM: Artificial Sequence
<220> FEATURE:
<223> OTHER INFORMATION: Cla-EGFP-Forward primer

<400> SEQUENCE: 29
gggcccaaaa tcgatgtgag caagggcgag gagct 35

<210> SEQ ID NO 30
<211> LENGTH: 38
<212> TYPE: DNA
<213> ORGANISM: Artificial Sequence
<220> FEATURE:
<223> OTHER INFORMATION: Sbf-EGFP-Reverse primer

<400> SEQUENCE: 30
gggcccaaac ctgcagggct tgtacagctc gtccatgc 38

<210> SEQ ID NO 31
<211> LENGTH: 35
<212> TYPE: DNA
<213> ORGANISM: Artificial Sequence
<220> FEATURE:
<223> OTHER INFORMATION: Cla-mGMCSF-Forward primer

<400> SEQUENCE: 31
gggcccaaaa tcgattggct gcagaattta ctttt 35

<210> SEQ ID NO 32
<211> LENGTH: 38

<212> TYPE: DNA
<213> ORGANISM: Artificial Sequence
<220> FEATURE:
<223> OTHER INFORMATION: Sbf-mGMCSF-Reverse primer

<400> SEQUENCE: 32
gggcccaaac ctgcagggtt tttggcctgg ttttttgc 38

<210> SEQ ID NO 33
<211> LENGTH: 20
<212> TYPE: DNA
<213> ORGANISM: Artificial Sequence
<220> FEATURE:
<223> OTHER INFORMATION: CVB3-Forward primer

<400> SEQUENCE: 33 tatacccct cccccaactg 20

<210> SEQ ID NO 34
<211> LENGTH: 20
<212> TYPE: DNA
<213> ORGANISM: Artificial Sequence
<220> FEATURE:
<223> OTHER INFORMATION: CVB3-Reverse primer

<400> SEQUENCE: 34
agcaagcatc cttggtggaa 20

<210> SEQ ID NO 35
<211> LENGTH: 63
<212> TYPE: DNA
<213> ORGANISM: Artificial Sequence
<220> FEATURE:
<223> OTHER INFORMATION: Sfi-AVFQ-Forward primer

<400> SEQUENCE: 35
ggggccggag gggccggact tagacaagca gtttttcaag gagctcaagt atcaacgcaa 60
aag 63

<210> SEQ ID NO 36
<211> LENGTH: 66
<212> TYPE: DNA
<213> ORGANISM: Artificial Sequence
<220> FEATURE:
<223> OTHER INFORMATION: Sfi-AVFQ-Reverse primer

<400> SEQUENCE: 36
ttgaaaaact gcttgtctaa gtccggcccc tccggccccc attttgctgt attcaactta 60
acaatg 66

<210> SEQ ID NO 37
<211> LENGTH: 40
<212> TYPE: DNA
<213> ORGANISM: Artificial Sequence
<220> FEATURE:
<223> OTHER INFORMATION: Sfi-EGFP-Forward primer

<400> SEQUENCE: 37
aaaaaaggcc tgagaggccg tgagcaaggg cgaggagctg 40

<210> SEQ ID NO 38
<211> LENGTH: 38
<212> TYPE: DNA
<213> ORGANISM: Artificial Sequence
<220> FEATURE:

<223> OTHER INFORMATION: Sfi-EGFP-Reverse primer

<400> SEQUENCE: 38
aaaaaaggcc tctctggcct tgtacagctc gtccatgc 38

<210> SEQ ID NO 39
<211> LENGTH: 43
<212> TYPE: DNA
<213> ORGANISM: Artificial Sequence
<220> FEATURE:
<223> OTHER INFORMATION: Sfi-mGMCSF-Forward primer

<400> SEQUENCE: 39
aaaaaaggcc tgagaggcct ggctgcagaa tttacttttc ctg 43

<210> SEQ ID NO 40
<211> LENGTH: 37
<212> TYPE: DNA
<213> ORGANISM: Artificial Sequence
<220> FEATURE:
<223> OTHER INFORMATION: Sfi-mGMCSF-Reverse primer

<400> SEQUENCE: 40
aaaaaaggcc tctctggcct tttggcctgg tttttg 37

<210> SEQ ID NO 41
<211> LENGTH: 85
<212> TYPE: DNA
<213> ORGANISM: Artificial Sequence
<220> FEATURE:
<223> OTHER INFORMATION: Inverse-2A-peptide-Fw primer

<400> SEQUENCE: 41
gagggcagag gaagtcttct aacatgcggt gacgtggagg agaatcccgg ccctggagct 60
caagtatcaa cgcaaaagac tgggg 85

<210> SEQ ID NO 42
<211> LENGTH: 55
<212> TYPE: DNA
<213> ORGANISM: Artificial Sequence
<220> FEATURE:
<223> OTHER INFORMATION: DLTTY-Fw primer

<400> SEQUENCE: 42
ccctgcaggg atcttacaac gtacggagct caagtatcaa cgcaaaagac tgggg 55

<210> SEQ ID NO 43
<211> LENGTH: 51
<212> TYPE: DNA
<213> ORGANISM: Artificial Sequence
<220> FEATURE:
<223> OTHER INFORMATION: CCEFAGLRQAVFQ-Fw primer

<400> SEQUENCE: 43
gccagagggg cctgctgcga gtttgcagga cttagacaag cagtttttca a 51

<210> SEQ ID NO 44
<211> LENGTH: 31
<212> TYPE: DNA
<213> ORGANISM: Artificial Sequence
<220> FEATURE:
<223> OTHER INFORMATION: Inverse-GMCSF-Rev primer

<400> SEQUENCE: 44
tttttggcct ggtttttgc attcaaaggg g 31

GENE-MODIFIED COXSACKIEVIRUS

TECHNICAL FIELD

The present invention relates to a modified coxsackievirus applicable to treatment of cancer. The present invention is useful in the field of oncolytic virotherapy.

BACKGROUND ART

Oncolytic virotherapy (cancer virotherapy) is a therapy in which a virus is allowed to infect cancer cells, and proliferate in cancer tissues to destroy and kill the cancer tissues by utilizing oncolytic property of the virus. Clinical studies are being conducted by using adenovirus and herpes simplex virus, which are DNA viruses, against brain tumor or breast cancer, and results showing safety and efficacy thereof are being reported.

Coxsackievirus group B type 3 (CVB3) (Non-patent documents 1 to 3) has a single strand plus-strand RNA genome, and proliferates only in the cytoplasm, and thus it hardly possibly introduce mutation into a host cell genome. Therefore, it is thought that it can be comparatively safely used in oncolytic virotherapy. Moreover, CVB3 is a common virus, and even if it infects, infection is limited to inapparent infection in many cases. However, there are reports concerning relevance thereof with aseptic meningitis, viral myocarditis, and pancreatitis. Marked oncolytic property of CVB3 against human non-small cell lung cancer has also been reported (Non-patent document 4).

As one of viruses of which application to the oncolytic virotherapy is expected, coxsackievirus group A type 21 (CVA21) is known (Patent document 1), and it has been reported that the virus was proliferated in a tissue-specific manner by incorporating miRNA into the virus genome (Non-patent document 5).

PRIOR ART REFERENCES

Patent Document

Patent document 1: Japanese Patent Unexamined Publication (KOHYO) No. 2007-527719

Non-Patent Documents

Non-patent document 1: Liu Z. et al., Virology, 265:206-17 (1999)

Non-patent document 2: Gauntt C. J. et al., Virus Res., 41:89-99 (1996)

Non-patent Document 3: Henke A. et al., Int. J. Med. Microbiol., 298:127-34 (2008)

Non-patent Document 4: Miyamoto S. et al., Cancer Res., 72 (10), 2609-21 (2012)

Non-patent document 5: Russell, S. J. et al., Nat. Med., 14 (11), 1278-83 (2008)

SUMMARY OF THE INVENTION

Object to be Achieved by the Invention

According to the studies of the inventors of the present invention, when wild-type CVB3 (CVB-WT) was evaluated in vivo, elevations of AMY, CK, AST and ALT were observed in serological tests, and destruction of exocrine tissues in the pancreas, inflammatory infiltration in the myocardium, and inflammatory infiltration in the liver were observed in histological diagnoses. It is desirable that these unfavorable actions are reduced.

Therefore, the inventors of the present invention attempted to insert a target sequence of tissue-specific microRNA (miRNA) into the 3' untranslated region (UTR) of the CVB3-WT genome, and expected that proliferation of the virus would be thereby suppressed in a tissue-specific manner, since, in a tissue containing miRNA, the RISC complex containing miRNA bound to the inserted target sequence to inhibit translation of virus proteins. In this attempt, the inventors of the present invention paid attention to two of miRNAs, of which use for similar purposes had not been so far examined at all. One is miR-217 considered to be specifically expressed in the pancreas, and the other one is miR-1 considered to be specifically expressed in muscular tissues and normal cells.

Further, during the examination of such insertion of a target sequence of specific miRNA into the genome as mentioned above, it was revealed that replication of the virus was inhibited depending on the position in 3' UTR at which the target sequence was inserted, and it is necessary to find an appropriate insertion position.

The inventors of the present invention also considered that a modified virus with further enhanced efficacy against tumors would be required for a case in which radical cure of tumor could not be realized with CVB3-WT.

Means for Achieving the Object

The present invention provides the followings.

[1] A modified coxsackievirus of which proliferation is suppressed in a tissue-specific manner, which comprises a mutated genome corresponding to genome of coxsackievirus B3 wild-type (CVB3-WT) inserted with at least one polynucleotide consisting of a target sequence of a tissue-specific microRNA (miRNA).

[2] The modified coxsackievirus according to 1, wherein insertion position is in the 3' UTR region of the CVB3-WT genome.

[3] The modified coxsackievirus according to 1 or 2, wherein the insertion position is a position upstream from the position 7344 or downstream from the position 7345 (preferably between the positions 7304 and 7305) of the CVB3-WT genome.

[4] The modified coxsackievirus according to any one of 1 to 3, wherein the tissue-specific miRNA is one expressed in pancreas and/or myocardium.

[5] The modified coxsackievirus according to any one of 1 to 4, wherein the tissue-specific miRNA consists of miR-1 and/or miR-217.

[6] The modified coxsackievirus according to any one of 1 to 5, wherein a plurality of (for example, 2 to 6) the polynucleotides consisting of the target sequence are inserted.

[7] The modified coxsackievirus according to any one of 1 to 6, wherein the inserted polynucleotide is the polynucleotide of the sequence of (a) or (b) mentioned below, or a polynucleotide of the sequence of (a) or (b) including deletion, substitution or addition of one to several nucleotides.

```
(a)
                                        (SEQ ID NO: 1)
ATA CAT ACT TCT TTA CAT TCC Acg atA TAC ATA

CTT CTT TAC ATT CCA acc ggt TCC AAT CAG TTC
```

-continued

```
CTG ATG CAG TAt cac TCC AAT CAG TTC CTG ATG
CAG TA
```

(b)

```
                                    (SEQ ID NO: 2)
TCC AAT CAG TTC CTG ATG CAG TAc gat TCC AAT
CAG TTC CTG ATG CAG TAa ccg gtT CCA ATC AGT
TCC TGA TGC AGT Atc acT CCA ATC AGT TCC TGA
TGC AGT A
```

[8] The modified coxsackievirus according to any one of 1 to 7, wherein a region encoding granulocyte-macrophage colony-stimulating factor (GM-CSF) is further inserted in an expressible form into the mutated genome.

[9] The modified coxsackievirus according to any one of 1 to 8, wherein a polynucleotide containing a region encoding GM-CSF and a region encoding a 2A protease recognition sequence ligated downstream is further functionally inserted into the mutated genome at a position downstream from ATG of the translation initiation point and upstream from VP4 region.

[10] The modified coxsackievirus according to 9, wherein the 2A protease recognition sequence is a sequence modified so as to be recognizable by 2A protease derived from poliovirus.

[11] A modified coxsackievirus having a mutated genome comprising CVB3-WT genome inserted with a region encoding GM-CSF in an expressible form.

[12] A modified coxsackievirus having a mutated genome comprising CVB3-WT genome functionally inserted with a polynucleotide containing a region encoding GM-CSF and a region encoding a 2A protease recognition sequence ligated downstream at a position downstream from ATG of the translation initiation point and upstream from VP4 region.

[13] The modified coxsackievirus according to 12, wherein the 2A protease recognition sequence is a sequence modified so as to be recognizable by 2A protease derived from poliovirus.

[14] A pharmaceutical composition containing the modified coxsackievirus according to any one of 1 to 13.

[15] The pharmaceutical composition according to 14, which is for a treatment (prophylactic or therapeutic treatment) of a cancer, preferably lung cancer, more preferably non-small cell lung cancer, or a precancerous state thereof.

[16] The modified coxsackievirus according to any one of 1 to 13 for use in a treatment (prophylactic or therapeutic treatment) of a cancer (preferably lung cancer, more preferably non-small cell lung cancer) or a precancerous state thereof.

[17] A method for a treatment (prophylactic treatment or therapeutic treatment) of a cancer (preferably lung cancer, more preferably non-small cell lung cancer) or a precancerous state thereof, which uses the modified coxsackievirus according to any one of 1 to 13, or the pharmaceutical composition according to 14 or 15.

[18] Use of a cell not showing high expression amount of a tissue-specific miRNA corresponding to the modified coxsackievirus according to any one of 1 to 13 (for example, H1299 cell) for titration or proliferation of the modified coxsackievirus.

[19] The pharmaceutical composition according to 14 or 15, which is a preparation for topical application or systemic administration.

Effect of the Invention

According to the present invention, safety and antitumor effect of a pharmaceutical composition using an enterovirus can be further enhanced.

BRIEF DESCRIPTION OF THE DRAWINGS

FIG. 1 A schematic diagram of CVB3 carrying a tissue-specific miRNA target sequence. The sequence shown in the diagram is inserted into pBluescript II-CVB3 at the position between 7304 and 7305 bp by the overlap extension PCR method.

FIG. 2 Difference in virus proliferation caused by difference of insertion position of the miRNA target sequence (HeLa cell).

FIG. 3 Difference in proliferation rate caused by difference in inserted sequence in modified CVB3 virus. CVB3-miR-1&217T slowed slower proliferation compared with the other two kinds. miR-1 was expressed in the HeLa cells used as a virus-producing cells, and it may be a cause of inhibition of the proliferation.

FIG. 4 Expression amounts of endogenous miRNA in cells of each type. The expression of miR-1 was markedly higher in the HeLa cells rather than the normal cells, BEAS-2B cells. The HeLa cells are unsuitable as modified virus-producing cells. It may be appropriate to use the H1299 cells showing low expression of both miRNAs as the production cells.

FIG. 5 miRNA-specific inhibition of virus proliferation. By introduction of exogenous miR-1 or miR-217 into the H1299 cells, virus proliferation of CVB3-miR-1&217T and CVB3-miR-217T was inhibited. This enabled miRNA-specific control of the proliferation using insertion of miRT.

FIG. 6 Difference in titer caused by difference in the production cells. By using the H1299 cells, genetically modified CVB3 showing a titer higher by 5 times or more can be produced.

FIG. 7 Difference in the titer caused by difference in cells used for the virus titer measurement. When the H1299 cells were used, a titer higher by 10 times or more was observed in the titration using the same virus. Therefore, the HeLa cells are unsuitable for the production of miRNA target sequence-carrying CVB3, and it is desirable to perform virus production and virus titer measurement in the H1299 cells.

FIG. 8 Non-clinical data concerning titer

FIG. 9 H&E tissue staining of pancreas

FIG. 10 Biochemical analyses

FIG. 11 $5^{th}$ Generation CVB3-infected cell

FIG. 12 $6^{th}$ Generation CVB3-infected cell

FIG. 13 The in vivo antitumor effect of genetically modified CVB3-GM-CSF was examined. A tumor (mouse lung cancer, TC-1 cells) was inoculated into the right abdominal part of C57BL/6 mouse on the day 0, and CVB3-WT or CVB3-GM-CSF was intratumorally administered every other day twice in total from the day 4 ($5\times10^6$ $TCID_{50}$/time).

FIG. 14 Sequences (SEQ ID NOS: 3 to 5) used for modification of $8^{th}$ generation CVB3

MODES FOR CARRYING OUT THE INVENTION

Figure 15:
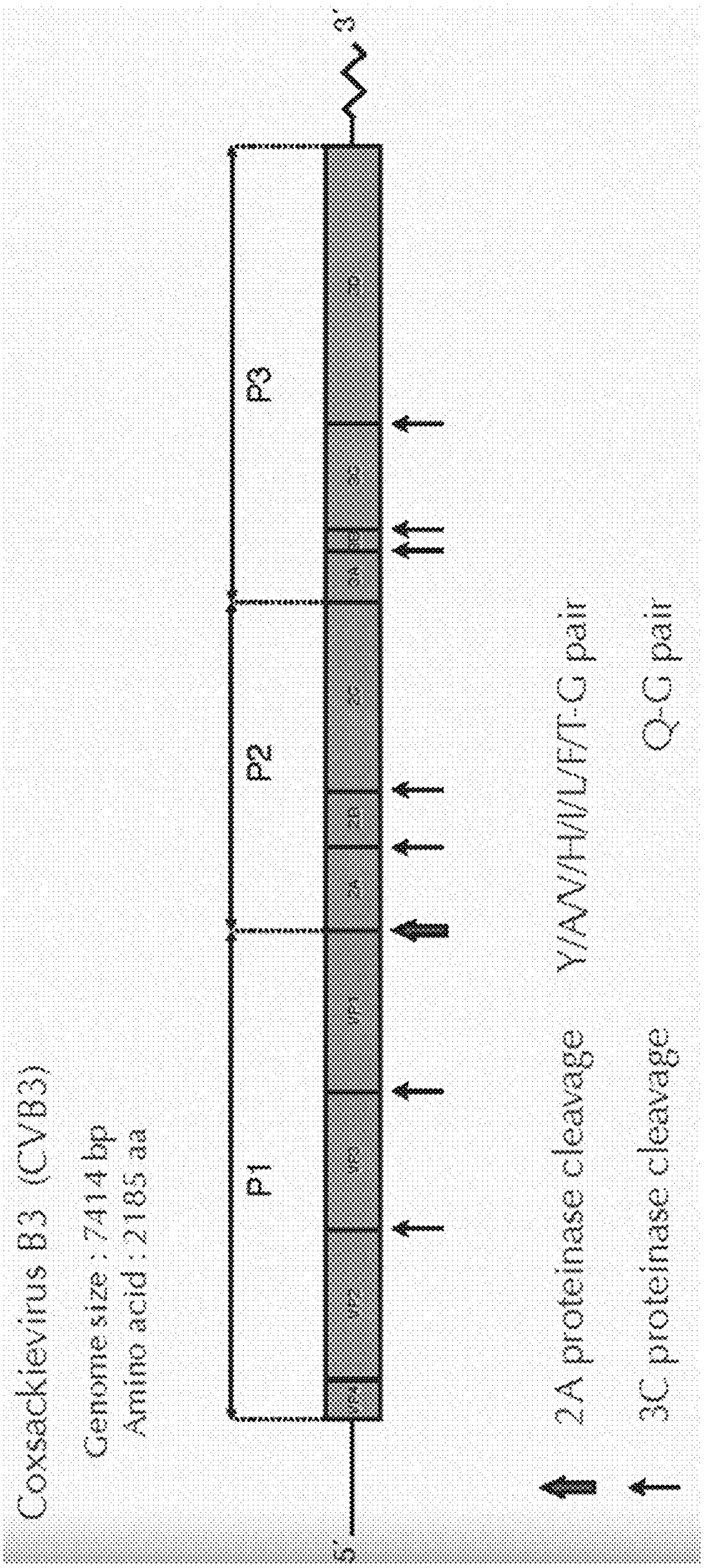
FIG. 15 Structures of the genome of CVB3-WT
Figure 16:
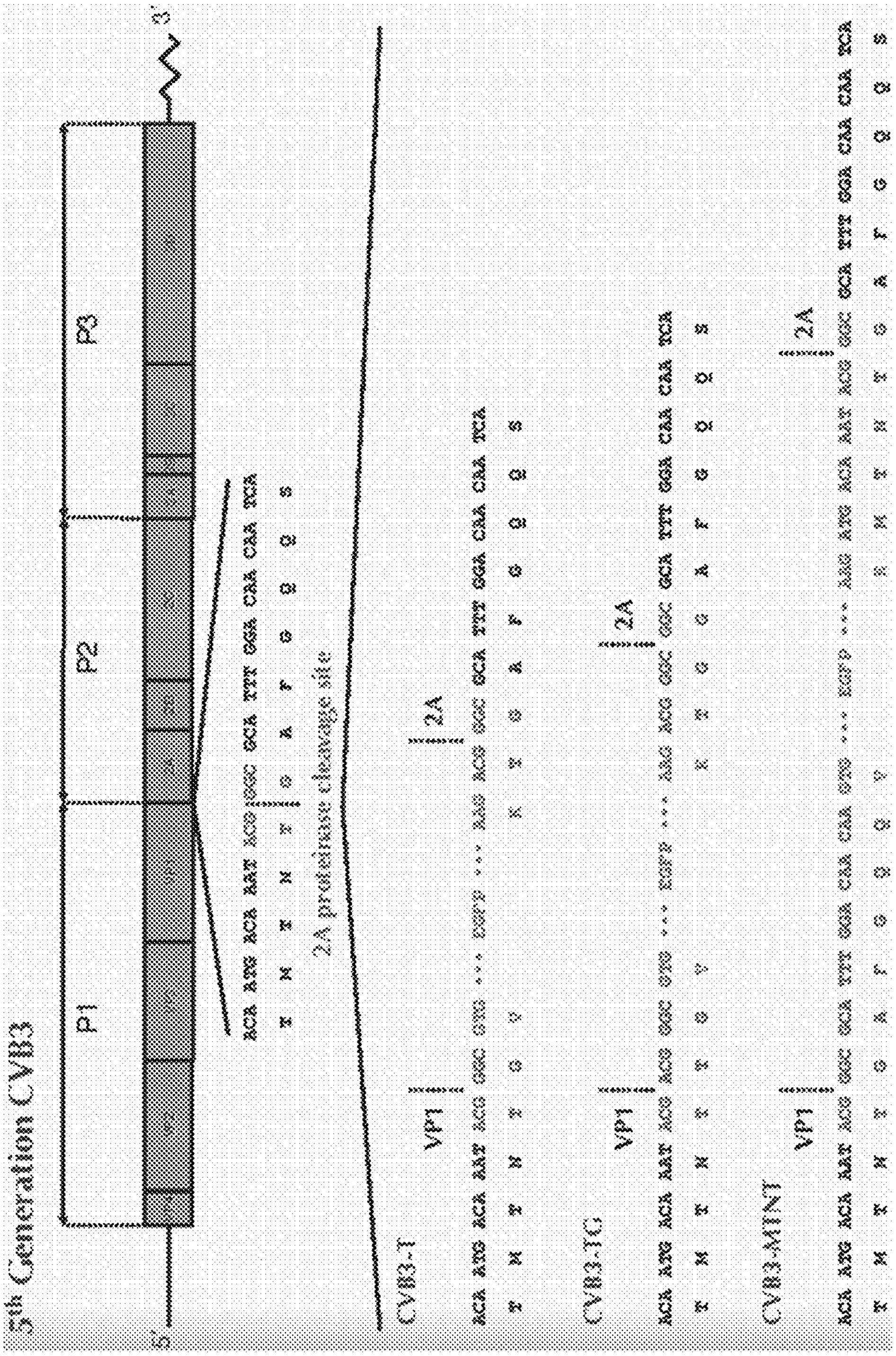
FIG. 16 Structures of $5^{th}$ generation CVB3 gene
Figure 17:
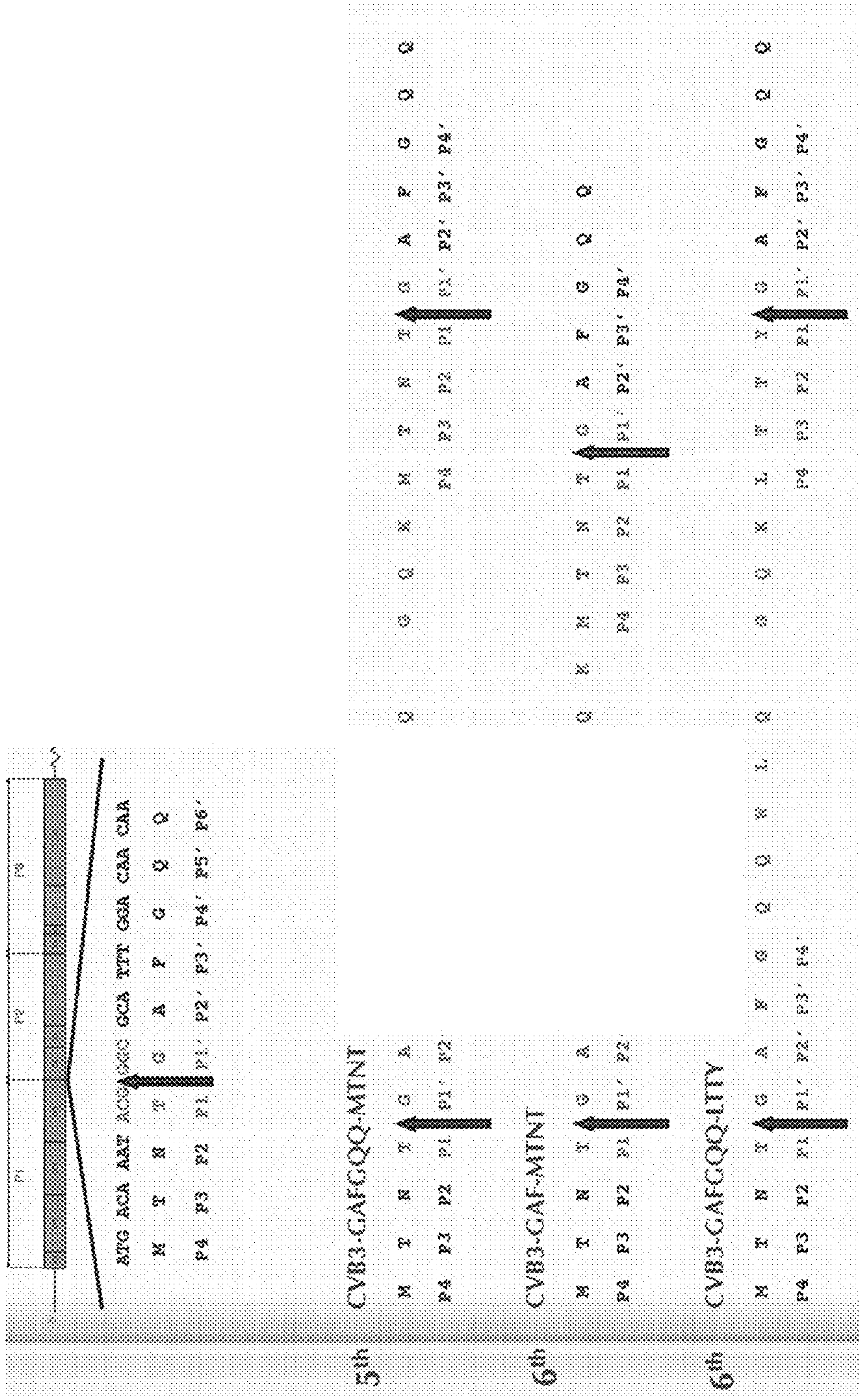
FIG. 17 Structures of $5^{th}$ generation and $6^{th}$ generation CVB3 genes FIG. 18 Structure of $8^{th}$ generation CVB3 gene
Figure 18:
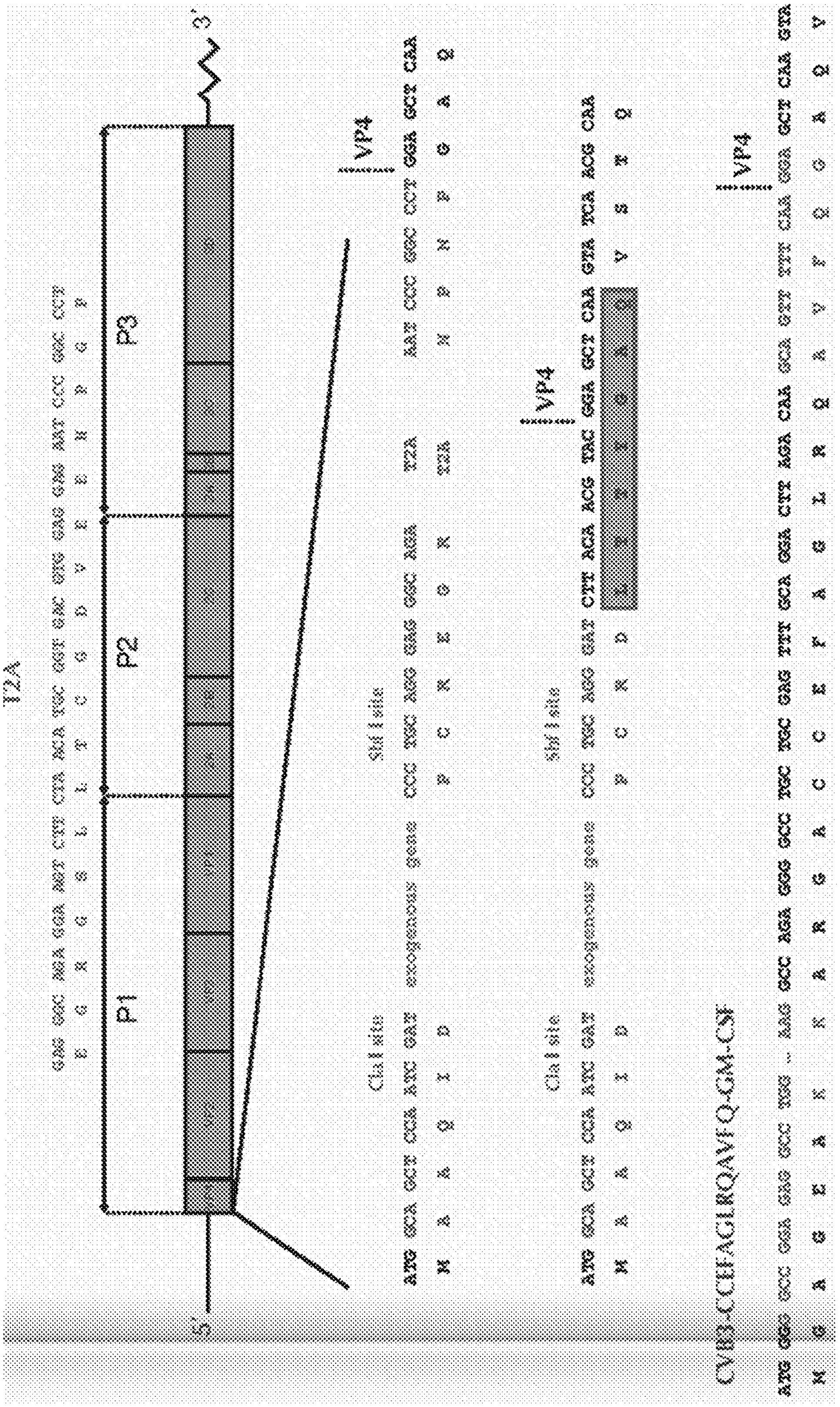

When a numerical value range is represented as "X to Y" in the present invention, the range includes the values X and Y as the minimum and maximum values. The expression "A and/or B" used in the present invention means at least one of A and B.

[Modified Coxsackievirus]

<Improvement in Safety of CVB3 by Insertion of miR Target Sequence>

One embodiment of the modified coxsackievirus provided by the present invention is a modified coxsackievirus containing a mutated genome consisting of the genome of coxsackievirus B3 wild-type (CVB3-WT) inserted with at least one polynucleotide comprising a target sequence of tissue-specific microRNA (miRNA). Proliferation of such a modified coxsackievirus may be suppressed in a tissue-specific manner.

The insertion position of the target sequence of the tissue-specific miRNA is preferably a position in the 3' UTR region of the CVB3-WT genome. According to the studies of the inventors of the present invention, genetically modified CVB3 inserted with the target sequence between 7304 and 7305 bp showed proliferation in the HeLa cells, which are common CVB3-producing cells, but genetically modified CVB3 inserted with the sequence between 7344 and 7345 bp did not show proliferation in the same cells. The same phenomenon was also seen in the HaLa cells in which expression of miRNA was suppressed. Therefore, the insertion position is more preferably a position upstream from the position 7344 or downstream from the position 7345 in the CVB3-WT genome, more preferably a position between the positions 7304 and 7305.

The tissue-specific miRNA (and the target sequence thereof) to be used can be variously chosen, so long as the intended effect is provided, but it is preferably miRNA expressed in the pancreas and/or myocardium (and the target sequence thereof). Particularly preferred examples of the tissue-specific miRNA are miR-1 and/or miR-217. One kind of tissue-specific miRNA (and the target sequence thereof) may be used, and a plurality of kinds of them may be used in combination.

The number of the target sequence of the tissue-specific miRNA to be inserted can be variously chosen, so long the intended effect is provided, but it is preferably 2 or larger, for example, 2 to 6.

In a particularly preferred embodiment, the inserted polynucleotide is the polynucleotide of the sequence of (a) or (b) mentioned below. Alternatively, it is a polynucleotide of the sequence of (a) or (b) that includes deletion, substitution or addition of one to several nucleotides, and can function in the same manner as that of the polynucleotide of the sequence of (a) or (b), that is, can suppress proliferation of a modified coxsackievirus constituted by inserting the polynucleotide into the 3' UTR region of the CVB3-WT genome in a tissue-specific manner. Alternatively, it is a polynucleotide that consists of a sequence showing a sequence identity of at least 90%, preferably 95%, more preferably 98%, still more preferably 99%, to the nucleotide sequence of (a) or (b), and can function in the same manner as that of the polynucleotide of the sequence of (a) or (b), that is, can suppress proliferation of a modified coxsackievirus constituted by inserting the polynucleotide into the 3' UTR region of the CVB3-WT genome in a tissue-specific manner.

```
(a)
                                            (SEQ ID NO: 1)
ATA CAT ACT TCT TTA CAT TCC Acg atA TAC ATA

CTT CTT TAC ATT CCA acc ggt TCC AAT CAG TTC

CTG ATG CAG TAt cac TCC AAT CAG TTC CTG ATG

CAG TA

(b)
                                            (SEQ ID NO: 2)
TCC AAT CAG TTC CTG ATG CAG TAc gat TCC AAT

CAG TTC CTG ATG CAG TAa ccg gtT CCA ATC AGT

TCC TGA TGC AGT Atc acT CCA ATC AGT TCC TGA

TGC AGT A
```

Methods for obtaining a polynucleotide consisting of a certain nucleotide sequence, but including deletion, substitution or addition of one to several nucleotides, and methods for calculating sequence identity (calculation can be performed by using, for example, BLAST algorithm) are well known to those skilled in the art.

<Improvement in Aggressiveness by Insertion of GM-CSF>

In another embodiment of the modified coxsackievirus provided by the present invention, a region encoding the granulocyte-macrophage colony-stimulating factor (GM-CSF) is inserted into the genome of CVB3-WT in an expressible form. In order to insert the region encoding GM-CSF in an expressible form, method for isolating mGM-CSF, insertion site of the gene, and modification of protease recognition sequence can be taken into consideration. Examples of the method for isolating mGM-CSF include use of 3C protease recognition sequence, use of 2A protease recognition sequence, use of IRES, and use of 2A peptide. Examples of the insertion site of the gene include a position immediately downstream from the translation initiation point ATG (upstream of VP4), a position upstream from the 2A gene, and 3' UTR of the genome of CVB3-WT. Examples of the modification of the protease recognition sequence include modification thereof into a sequence derived from a virus other than CVB3.

According to one of the preferred embodiments, a polynucleotide including the region encoding GM-CSF, and the region encoding the 2A protease recognition sequence ligated downstream is functionally inserted at a position downstream from ATG of the translation initiation point and upstream from the VP4 region.

The structure of the genome of CVB3-WT is shown in FIG. 15.

According to one embodiment of the present invention, as for the recognition sequence of 2A protease (also referred to as "$2A^{pro}$"), it is preferable to use a sequence modified into a sequence that can be recognized by the 2A protease of poliovirus, rather than to use one derived from CVB3.

In a particularly preferred embodiment, the polynucleotide to be inserted is a polynucleotide consisting of the nucleotide sequence of SEQ ID NO: 4, or a polynucleotide that comprises the sequence of any one of SEQ ID NOS: 3 to 5, preferably the sequence of SEQ ID NO: 4, including deletion, substitution or addition of one to several nucleotides, and can function in the same manner as that of the sequence of SEQ ID NO: 4, that is, can express GM-CSF, and exhibit cytopathogenic effect (CPE) when it is inserted into the CVB3-WT genome to constitute a modified coxsackievirus.

Alternatively, it is a polynucleotide that consists of a sequence showing sequence identity of at least 90%, preferably 95%, more preferably 98%, further preferably 99%, to the nucleotide sequence of any one of SEQ ID NOS: 3 to 5, preferably the sequence of SEQ ID NO: 4, and can function in the same manner as that of the sequence of SEQ ID NO: 4, that is, can express GM-CSF, and exhibit cytopathogenic effect (CPE) when it is inserted into the CVB3-WT genome to constitute a modified coxsackievirus.

Modification for improving aggressiveness against cancer by insertion of such a polynucleotide encoding GM-CSF or the like may be performed independently, or may be performed in combination with insertion of the aforementioned miRNA target sequence. In a particularly preferred embodiment of the present invention, the miRNA target sequence and the polynucleotide encoding GM-CSF are inserted in combination, since high safety and high oncolytic property can be expected.

<Preparation of Modified Virus Etc.>

The modified virus of the present invention can be prepared by genetically manipulating CVB3-WT. CVB3-WT can be isolated from a sample or the like by a known virus isolation method. Examples of the virus isolation method include centrifugation, proliferation of the virus in cultured cells, and so forth. If a modified coxsackievirus is once prepared, the modified coxsackievirus can be proliferated by using various biological methods for production of virus.

CVB3 to be modified may be obtained by biological selection, which is performed by subculturing a naturally occurring virus many times in a cell strain so that the virus acquires high infection ability for cancer cells. Examples of cell strain suitable for the biological selection include cancer cell strains that express CAR, DAF and so forth.

The modified coxsackievirus prepared according to the present invention can be evaluated for various aspects such as safety, efficacy, and titer by various in vitro or in vivo means well known to those skilled in the art. For example, aggressiveness against cancer cells (oncolytic property or toxicity) can be confirmed by examining survival of a cancer cell strain exposed to CVB3. Examples of the method for examining survival of a cell strain include, for example, a method of staining immobilized cells with a staining solution, and counting stained live cells, the crystal violet method, a method of quantifying an apoptosis-specific marker, and so forth. By quantifying cancer cells of a cell strain surviving after a predetermined time of incubation with CVB3 using any of the aforementioned methods, cancer cells killed by the cytotoxicity provided by the infection with CVB3 can be quantified as a result.

When the inventors of the present invention produced modified CVB3 (inserted with miRNA target sequence), and measured titer thereof by using the HeLa cells, and H1299 cells, which showed low expression of the miRNA used, the modified CVB3 produced in the H1299 cells showed a virus titer even 5 times higher than that of the modified CVB3 produced in the HeLa cells under the conditions described in the section of examples in this specification. Further, when virus titer of the modified CVB3 produced in the HeLa cells was measured in the H1299 cells and the HeLa cells, the virus titer observed in the H1299 cells was 10 times or more times higher than the virus titer observed in the HeLa cells. Therefore, according to one embodiment of the present invention, the H1299 cells are suitable for the production of the modified virus and virus titer measurement. According to the present invention, it is proposed, for the titer measurement or proliferation of the modified coxsackievirus, to use a cell not showing a large expression amount of corresponding tissue-specific miRNA (for example, H1299 cell).

[Pharmaceutical Composition]

<Indication of Treatment>

One embodiment of the pharmaceutical composition provided by the present invention contains the aforementioned modified CVB3 as an active ingredient. Type of cancer as an object of the treatment with the pharmaceutical composition is not particularly limited, and it may be a solid cancer or humoral cancer. CVB3 shows cytotoxicity against cancer cell of solid cancer and humoral cancer. The cytotoxicity of CVB3 against cancer cells is based on lysis of cancer cells provided when the virus infects the cancer cells and replicates in the cytoplasm of the cancer cells, or apoptosis induced by activation of caspase in the cancer cells caused by infection of the virus. CVB3 can recognize CAR on the cell surface, and infect the cell. The "treatment (to treat)" referred to in the present invention for a disease or condition include a prophylactic treatment and therapeutic treatment.

CVB3 has cytotoxicity against cancer cells of solid cancer and humoral cancer. Solid cancer cells for which especially potent cytotoxicity is induced are cells of a cancer selected from the group consisting of small cell lung cancer, non-small cell lung cancer, lung squamous cell cancer, malignant mesothelioma, colon cancer, colorectal cancer, esophageal cancer, hypopharyngeal cancer, human B lymphoma, breast cancer, and uterine cervix cancer. Therefore, the pharmaceutical composition of this embodiment is preferably applied to any one selected from the group consisting of small cell lung cancer, non-small cell lung cancer, lung squamous cell cancer, malignant mesothelioma, colon cancer, colorectal cancer, esophageal cancer, hypopharyngeal cancer, human B lymphoma, breast cancer, and uterine cervix cancer, as an object.

Lung cancer is a cancer of which number of affected individuals takes higher rank. The pharmaceutical composition of this embodiment would be able to contribute to the treatment of more lung cancer patients. Morbidities of colon cancer and colorectal cancer are increasing in Japan where the Western eating habits were established, and mortalities are also increasing. The pharmaceutical composition of this embodiment increases the choices of therapeutic drug for colon cancer and colorectal cancer, and it is beneficial to the patients. The recurrence rate of esophageal cancer after surgical resection is as high as 30 to 50%, and the sensitivity thereof to the existing drugs is low. It is expected that the pharmaceutical composition of this embodiment improves the treatment results of esophageal cancer.

Further, the pharmaceutical composition of this embodiment shows potent cytotoxicity against cancer cells resistant to CDDP, gefitinib, or oxaliplatin. Therefore, a treatment effective to so-called intractable cancers that show resistance to these anticancer agents can be provided.

The pharmaceutical composition of this embodiment shows potent cytotoxicity also against cancer stem cells, when the composition contains CVB3. Cancer stem cells are considered to be one of the causes of relapse of cancer, and therefore the composition is useful for prevention of metastasis and relapse of cancer.

<Dosage Form, Usage, and Dose>

The pharmaceutical composition of this embodiment can be in various dosage forms, and can be administered via various administration routes. That is, the pharmaceutical composition of this embodiment can also be a topical preparation, or a preparation for systemic administration.

For example, it can be administered as an injection or fusion drip by intratumorale administration, intravenous administration, intrathoracic administration, or intraperitoneal administration according to type of cancer. In particular, in the many cases of gastrointestinal cancers such as esophageal cancer and colon cancer, the pharmaceutical composition can be directly injected into a tumor tissue with visually observing the tumor tissue with an endoscope, or the like. In such a case, since the injection site can be confirmed with an endoscope, or the like, there is also provided an advantage that even if bleeding is observed, it is easily treated. Otherwise, it may be administered by oral administration, or it may be intramuscularly or subcutaneously administered, or administered via rectum, vagina, nasal cavity, or the like.

The pharmaceutical composition of this embodiment may contain a carrier, diluent, auxiliary agent etc., in addition to the modified CVB3. As the carrier, for example, liposome, micelle, and so forth are preferred. The liposome contains a combination of a lipid and a steroid or steroid precursor that contributes to membrane stability. Examples of the lipid include phosphatidyl compounds such as phosphatidylglycerol, phosphatidylcholine, phosphatidylserine, sphingolipids, phosphatidylethanolamine, cerebroside, and ganglioside. With CVB3 contained in liposome or micelle, immune response of a host can be reduced.

Examples of the diluent include, for example, desalted water, distilled water, physiological saline, and so forth. Examples of the auxiliary agent include vegetable oils, cellulose derivatives, polyethylene glycol, fatty acid esters, and so forth.

In the case of oral administration, the pharmaceutical composition may contain a sweetener, disintegrating agent, diluent, coating agent, preservative, and so forth.

The pharmaceutical composition of this embodiment is administered so that the amount of CVB3 is a sufficient for treatment of cancer. Dose is determined on the basis of weight, age, sex of patients, size of tumor tissue, and so forth. For example, when the pharmaceutical composition is used as a solution, it is sufficient that $1\times10^2$ to $1\times10^{10}$ 50% tissue culture infectious dose ($TCID_{50}$) of CVB3, preferably $1\times10^5$ $TCID_{50}$ or more of CVB3, is contained in 1 ml of the solution. The pharmaceutical composition may be administered at a single time, or may be administered at a plurality of times. The pharmaceutical composition may be continuously administered as a sustained release preparation.

<Combinatory Use with Other Preparation>

The pharmaceutical composition of this embodiment may be used together with an anticancer agent. When an anticancer agent of which action mechanism is different from that of the pharmaceutical composition is used in combination, improvement in the antitumor effect can be expected. Although the anticancer agent is not particularly limited, those used for a treatment of small cell lung cancer, non-small cell lung cancer, lung squamous cell cancer, malignant mesothelioma, colon cancer, colorectal cancer, esophageal cancer, hypopharyngeal cancer, human B lymphoma, uterine cervix cancer, pancreatic cancer, and so forth are desirable. Specific examples of the anticancer agents are CDDP (cisplatin), gefitinib, oxaliplatin, and so forth.

[Others]

The pharmaceutical composition of this embodiment of the invention may contain a polynucleotide derived from CVB3 (including modified CVB3, the same shall apply to the following descriptions) that can infect a cancer cell as an active ingredient. The polynucleotide derived from CVB3 may be virus RNA directly isolated from CVB3, synthetic RNA, or cDNA corresponding to a nucleotide sequence of isolated virus RNA. For isolating virus RNA, an arbitrary method can be used. Examples of the method of isolating virus RNA include, for example, a method based on use of phenol/chloroform extraction, and so forth. The polynucleotide may be a virus plasmid or expression vector containing a polynucleotide for producing the virus. Such an expression vector includes, for example, a plasmid that can express RNA encoding a virus protein required for producing the virus. The expression vector may contain a transcription control sequence functionally ligated with the inserted polynucleotide. The transcription control sequence referred to here is, for example, a promoter for starting transcription, an expression control element for enabling binding of ribosome to the transcribed mRNA, or the like.

As the expression vector, for example, pSV2neo, pEF-PGk, puro, pTk2, non-replicable adenovirus shuttle vector, cytomegalovirus promoter, etc. can be used. cDNA encoding a virus protein required for producing virus can be prepared by reverse transcription of a virus RNA or a fragment thereof.

The pharmaceutical composition of this embodiment may contain, for example, a carrier such as liposome, in addition to the polynucleotide derived from CVB3 that can infect a cancer cell. The polynucleotide derived from CVB3 may contain, for example, the polynucleotide consisting of the sequence of SEQ ID NO: 1 or 2, and/or a polynucleotide consisting of any of the sequences of SEQ ID NOS: 3 to 5.

Hereafter, examples of the present invention will be explained. However, the scope of the present invention is not limited by these examples.

Examples

I. Improvement in Safety of CVB3 by Insertion of miRNA Target Sequence

The object of this research is reduction of the adverse reaction of oncolytic wild-type CVB3 (CVB-WT) observed in the pancreas and myocardium. CVB3-WT causes especially intense inflammation in the pancreas, and there are confirmed marked elevation of AMY in a serobiochemical test and destruction of exocrine glands in H&E stained tissue images. In order to overcome these problems, the inventors of the present invention inserted a target sequence of tissue-specific microRNA (miRNA) into the genome 3' untranslated region (UTR) of CVB3-WT with aiming at achieving the expected reduction of adverse reaction. Since the RISC complex having a tissue-specific miRNA binds to the inserted target sequence of miRNA to inhibit translation of virus protein etc., tissue-specific suppression of the proliferation is enabled.

I-1. Difference in Virus Proliferation Caused by Difference in Insertion Site of Target Sequence The inventors of the present invention paid attention to two kinds of miRNAs, i.e., one is miR-217 considered to be specifically expressed in the pancreas, and the other one is miR-1 considered to be specifically expressed in muscular tissue and normal cells, and combined them to prepare two kinds of miRNA target sequences consisting of four of continuously ligated miRNA target sequences (miR-1×2&miR-217×2, and miR-217×4). The two kinds of target sequences were each inserted into the CVB3 genome between 7304 and 7305 bp by using the overlap extension PCR method. The aforementioned target sequences were also inserted into the CVB3 genome between 7344 and 7345 bp by the overlap extension PCR method (FIG. 1).

For both the genetically modified CVB3 (CVB3-miR-1&217T, and CVB3-miR-217T) in which the insertion was made between 7304 and 7305 bp, proliferation was observed in the HeLa cells, which are common CVB3-producing cells, and thus genetically modified CVB3 could be successfully produced. However, for both the genetically modified CVB3 in which the insertion was made between 7344 and 7345 bp, proliferation was not observed in the HeLa cells (FIG. 2). Further, the same phenomenon was also observed in the HaLa cells in which expression of miRNA was suppressed, and therefore it became clear that CVB3 may not replicate depending on the insertion site of the miRNA target sequence, even if it is inserted into 3' UTR, and these 40 bp constitute a sequence important for the replication of CVB3.

Russell et al. previously reported that when a miRNA target sequence was inserted into 3' UTR of CVA21, tissue-specific suppression of proliferation was induced. However, research of the inventors of the present invention is novel in that they paid attention to miRNAs different from those mentioned by Russell et al., and they used novel miRNAs for which insertion into viral genome has not been reported. In addition, Russell et al. did not refer to at which site of 3' UTR the insertion should be made to obtain good result, and the finding that the insertion between 7304 and 7305 bp allows normal replication of CVB3 is also considered to be novel.

The term genetically modified CVB3-miRT henceforth refers to one in which the insertion was made between 7304 and 7305 bp. Further, CVB3-miR-1&217T refers to the modified CVB3 inserted with two each of miR-1 and miR-217T shown in FIG. 1 (polynucleotide of SEQ ID NO: 1), and CVB3-miR-217T refers to the modified CVB3 inserted with four of miR-217T shown in FIG. 1 (polynucleotide of sequence of SEQ ID NO: 2), unless especially indicated.

I-2. Difference in Proliferation Rate Caused by Difference of Insertion Sequence and Expression Amount of Endogenous miRNA in Various Cells When the genetically modified CVB3-miRT was produced by using the HeLa cells, retardation of proliferation was observed only for CVB3-miR-1&217T compared with the other two kinds (CVB3-WT, CVB3-miR-217T) (FIG. 3).

Since it was expected from this result that miR-1 was expressed in a large amount in the HeLa cells, expression amounts of endogenous miRNA were quantified by the real-time PCR method in the HeLa cells, BEAS-2B cells, which are normal respiratory epithelium cells, cells of lung cancer cell strains as the objects of treatment (A549 cells, NCI-H1299 cells), AsPC-1 cells, which are cells of pancreatic cancer cell strain, and RD cells, which are malignant rhabdomyoma cells. As a result, it was revealed that the expression amount of miR-1 in the HeLa cells was 20 times or more higher than that observed in the BEAS-2B cells as normal cells, as expected, and the expression amount in the HeLa cells was the second highest following that observed in the RD cells of the malignant rhabdomyoma cell strain. In the cells of both the two kinds of lung cancer cell strains, which are the object of the treatment, expressions of miR-1 and miR-217 were hardly observed (FIG. 4).

Since the above results suggested a possibility of miRNA-specific proliferation suppression of the genetically modified CVB3-miRT of the present invention, miR-1 and miR-217 were introduced by transfection into the NCI-H1299 cells, in which expressions of miR-1 and miR-217 were hardly seen, and it was examined whether suppression of proliferation of CVB3-miRT would be seen. As a result, it was revealed that, in the H1299 cells introduced with miR-1, the oncolytic effect could not be seen for CVB3-miR-1&217T, even when CVB3-miR-1&217T was infected in a 100 times larger amount compared with CVB3-WT (FIG. 5A). Further, in the H1299 cells introduced with miR-217, the oncolytic effect was not seen for CVB3-miR-1&217T and CVB3-miR217T, even when they were infected in a 10,000 times larger amount compared with CVB3-WT (FIG. 5B). These results revealed that the genetically modified CVB3 caused RNA interference in a target miRNA-specific manner to show suppression of proliferation.

I-3. Difference in Titer Provided by Difference of Cells for Production and Titration In order to determine cells appropriate for producing CVB3-miRT in consideration of the aforementioned results, virus production and measurement of the titer were performed by using the HeLa cells, and the H1299 cells, in which expression of miRNA was low. CVB3-miR-1&217T produced in the H1299 cells showed a virus titer even 5 times higher than that of the virus produced in the HeLa cells (FIG. 6). Further, when the virus titer of CVB3-miR-1&217T produced in the HeLa cell was measured in the H1299 cells and the HeLa cells, the virus titer observed in the H1299 cells was 10 times or more higher than the virus titer observed in the HeLa cells (FIG. 7). These results revealed that the H1299 cells are suitable for virus production and virus titer measurement of CVB3-miRT.

I-4. In Vivo Test

In vivo antitumor effect and toxicity of the genetically modified CVB3 were examined. A tumor (non-small cell lung cancer, NCI-H1299 cells) was inoculated into the right abdominal parts of nude mice on the day 0, and the CVB3 virus was intratumorally administered from the day 2 every other day, 5 times in total ($5\times10^6$ $TCID_{50}$/time).

As a result, the tumor volume ($mm^3$) was suppressed in the CVB3-WT-administered group and CVB3-miRT-administered group (destruction of exocrine glands in the pancreas, inflammatory infiltration in the myocardium, and inflammatory infiltration in the liver were observed in histological diagnoses in CVB3-WT-administered group, FIGS. 8A and 8B). Forty days after the inoculation of tumor, whereas the survival rate of the non-treated group was 0%, the survival rate of the virus-administered group was 100% (FIG. 8C).

Further, when serum amylase (AMY), creatine kinase (CK), and aspartate aminotransferase (AST) were measured, slightly high values were observed in the CVB3-WT-administered group, but in the CVB3-miRT administered group, the values were comparable to those observed for the non-treated group (FIG. 9). Further, in the H&E tissue staining of the pancreas, particular destruction of the exocrine glands, which may be caused by administration of CVB3-WT, was not seen (FIG. 10). These results suggested that CVB3-miR-1&217T hardly influences on the pancreas, muscle, and liver.

I-5. Methods Summary

This research was performed according to the following protocols.

[Production of CVB3-miRT]

<Construction of Vector>

(Materials and Reagents)

CVB3 Plasmid
KOD -Plus-
UltraPure
Primers

```
CVB3-miR-Forward
(20 pmol/µl, SEQ ID NO: 6)
caggtctttgaggggaacaa

CVB3-miR-Reverse
(20 pmol/µl, SEQ ID NO: 7)
attaatgcagctggcacgac
```

-continued

```
miR-1&217T Forward
(20 pmol/μl, SEQ ID NO: 8)
ttaATACATACTTCTTTACATTCCAcgatATACATACTTCTTT

ACATTCCAaccggtTCCAATCAGTTCCTGATGCAGTAtcacTC

CAATCAGTTCCTGATGCAGTAgagacaatttgaaataatttag

miR-1&217T Reverse
(20 pmol/μl)
                                  (SEQ ID NO: 9)
ctcTACTGCATCAGGAACTGATTGGAgtgaTACTGCATCAGGA

ACTGATTGGAaccggtTGGAATGTAAAGAAGTATGTATatcgT

GGAATGTAAAGAAGTAGTATtaatctaaaaggagtccaacca

miR-217T Forward
                                 (SEQ ID NO: 10)
ttaTCCAATCAGTTCCTGATGCAGTAcgatTCCAATCAGTTCC

TGATGCAGTAaccggtTCCAATCAGTTCCTGATGCAGTAtcac

TCCAATCAGTTCCTGATGCAGTAgagacaatttgaaataattt

ag
```

(Methods)

The following components are mixed in the following order in a 0.2-ml PCR tube on ice.

TABLE 1

| Reagent | First half | Second half |
|---|---|---|
| UltraPure | 34 μl | 34 μl |
| 10× Buffer for KOD -Plus- | 5 μl | 5 μl |
| 2 mM dNTPs | 5 μl | 5 μl |
| 25 mM $MgSO_4$ | 2 μl | 2 μl |
| Plasmid | 1 μl | 1 μl |
| Primer Forward | CVB3-miR-Forward | Arbitrary miRT-Forward |
| Primer Reverse | Arbitrary miRT-Reverse | CVB3-miR-Reverse |
| KOD -Plus- | 1 μl | 1 μl |

2. The mixture is stirred by tapping or gentle pipetting, and gently spun down, and the solution is collected.

The following program is executed with a thermal cycler (Bio-Rad).

3. 94° C. 2:00, 94° C. 0:15, 62° C. 0:15, 68° C. 1:30 (10 cycles), 72° C. 7:00

4. Overlap extension PCR is performed by using the two PCR products.

5. These two PCR products are each put into a tube in a volume of 1 μl, and used as the template together with the CVB3-miR-Forward and CVB3-miR-Reverse primers to perform PCR. The aforementioned program is executed for 30 cycles.

6. The overlap extension PCR product is purified, and the product and the CVB3 plasmid are treated with the restriction enzymes Sail and BstII.

7. Agarose gel electrophoresis is performed with the product obtained after the restriction enzyme treatment, and target bands are excised.

8. After the gel purification, the CVB3 plasmid treated with the restriction enzymes and the overlap extension PCR product treated with the restriction enzymes are reacted at 16° C. for 2 hours by using Ligation High.

9. The ligation product is introduced into competent cells, and the cells are cultured at 37° C.

10. Colonies are picked up on the next day, and cultured in LB medium.

11. Plasmids are collected from the culture, and insertion of the miRNA target sequence is confirmed.

<Preparation of Virus RNA>

(Materials and Reagents)

MEGAscript (registered trademark) Kit (Ambion, Cat# AM1333, stored at −20° C.)

CVB3 plasmids (CVB3-WT, CVB3-miR-1&217T, CVB3-miR-217T)

Phenol:Chloroform 5:1, Acid-equilibrated, pH 4.7 (Sigma Cat# P1944-100ML, Lot#010M1574)

Chloroform (Nacalai Tesque, Cat#08402-55, Lot# V6K0595)

75% Ethanol (using nuclease-free water)

10 mol/l Ammonium Acetate Solution (Nacalai Tesque, Cat#02432-74, Lot# L2B2291)

UltraPure (Methods)

1. The regents are mixed at room temperature in the following order in a 0.2-ml PCR tube (total 20 μl).

TABLE 2

| Reagent | Volume |
|---|---|
| Linear template DNA (0.1-1 μg) | x μl |
| Nuclease-free Water | (8-x) μl |
| ATP solution | 2 μl |
| CTP solution | 2 μl |
| GTP solution | 2 μl |
| UTP solution | 2 μl |
| 10× Reaction Buffer | 2 μl |
| Enzyme Mix | 2 μl |
| Total | 20 μl |

2. Reaction is allowed at 37° C. for 3 hours by using a thermal cycler (thermal cycler of Bio-Rad is used).

3. After 3 hours, TURBO DNase (1 μl) is added to the tube during the reaction, the mixture is sufficiently stirred, and the reaction is further allowed at 37° C. for 15 minutes.

4. A solution is prepared in advance by mixing 114 μl of UltraPure and 15 μl of attached Ammonium Acetate Stop Solution in 1.5-ml tubes in a number of required number ×1.1.

5. After the reaction, 129 μl of the aforementioned mixture is added to the tubes, and pipetting is performed.

6. The whole volume of the mixture is transferred to a 0.7-ml tube.

7. Phenol:Chloroform (150 μl) is added to the mixture, and the mixture is stirred by pipetting and inverting the tube.

8. The mixture is centrifuged at 10,000×g for 2 minutes at room temperature.

9. The supernatant (about 150 μl) is transferred to another new 0.7-ml tube.

10. Chloroform (150 μl) is added to the aqueous layer, and the mixture is stirred by inverting the tube.

21. The mixture is centrifuged at 10,000×g for 2 minutes at room temperature.

22. The supernatant (about 100 μl) is transferred to another new 0.7-ml tube.

23. Cold 5 M Ammonium acetate (150 μl) is added to the aqueous layer, and the mixture is stirred by pipetting.

24. The mixture is left standing on ice for 10 minutes.

25. The mixture is centrifuged at 10,000×g for 15 minutes at 4° C.

26. The supernatant is slowly removed with Pipetman.

27. 75% Ethanol (200 μl) is gently added to the mixture.

28. The mixture is centrifuged at 10,000×g for 10 minutes at 4° C.

29. The supernatant is removed as much as possible with Pipetman.
30. UltraPure (70 μl) is added to the pellet to dissolve it.
<Preparation of Virus>
(Materials and Reagents)
NCI-H1299 cells ($1\times10^7$ cells/150 mm/dish)
RPMI 1640 w/10% FBS (growth medium)
Opti-MEM (registered trademark) I
Lipofectamine™ 2000 Reagent (Invitrogen, Cat#11668-019)
In vitro transcription product
(Methods)
1. RNA (80 μg) is added to Opti-MEM contained in a tube, and Lipofectamine 2000 (120 μl) is added to Opti-MEM contained in another tube.
2. Both the tubes are left standing at room temperature for 5 minutes.
3. The contents of both the tubes are mixed, and left standing at room temperature for 20 minutes.
4. After 20 minutes, the whole volume of the mixture is added to the NCI-H1299 cells.
5. After 4 hours, the mixture is replaced with the growth medium.
6. The cells were incubated at 37° C. for 24 hours in 5% $CO_2$.
7. Twenty-four hours after the transfection, the NCI-H1299 cells are scraped with a cell scraper without discarding the medium.
8. The supernatant is collected together with the cells in a 50-ml tube.
9. The 50-ml tube is immersed into liquid $N_2$ to freeze the content.
10. The content is thawed on a water bath at 37° C.
11. Freezing and thawing of 9 and 10 are repeated twice (3 cycles in total of freezing and thawing).
12. The content is centrifuged at 3,000 rpm for 15 minutes at 4° C.
13. The medium of the NCI-H1299 cells, to which the supernatant is to be transferred, is replaced with fresh medium (15 ml)
14. The whole volume of the centrifuged supernatant is added to the NCI-H1299 cells.
15. The cells are incubated at 37° C. for 5 to 6 hours in 5% $CO_2$.
16. When CPE of 60 to 70% or higher is confirmed, the culture supernatants is removed.
17. Opti-MEM (registered trademark) I (2 ml) is added.
18. The cells are scraped with a cell scraper.
19. The whole volume of Opti-MEM (registered trademark) I is collected together with the cells into a 15-ml tube.
20. The 15-ml tube is immersed into liquid nitrogen to freeze the content (about 2 minutes).
21. The content is thawed on a water bath at 37° C. (about 10 minutes).
22. Freezing and thawing of 20 and 21 are repeated twice (3 cycles in total of freezing and thawing).
23. The content is centrifuged at 3,000 rpm for 15 minutes at 4° C.
24. The supernatant is stored at −80° C.
<Measurement of Virus Titer>
(Materials and Reagents)
96-Well plate (flat bottom)
NCI-H1299 cells ($5\times10^3$ cells/100 μl/well)
RPMI 1640 w/10% FBS (growth medium)
96-Well plate (round bottom)
Opti-MEM (registered trademark) I
(Methods)
1. The NCI-H1299 cells are inoculated into all the wells of the 96-well flat plate in an amount of $5\times10^3$ cells/100 μl/well.
2. The cells are incubated at 37° C. for 7 hours in 5% $CO_2$.
3. Opti-MEM is added in a volume of 180 μl each to the wells of the second row to the final row of the 96-well round plate.
4. For the highest virus concentration (usually $10^{-2}$) in the wells of the first row, Opti-MEM (990 μl) is added to a 1.5-ml tube, the virus stock solution (10 μl) is added to the tube, and the mixture is stirred by sufficient pipetting to prepare $10^{-2}$ solution.
5. The $10^{-2}$ virus solution is added in a volume of 120 μl each to the wells of the first row of the 96-well round plate.
6. The virus solution in the wells of the first row is moved in a volume of 20 μl each to the wells of the second row by using an 8-tip electric pipetter.
7. Pipetting is performed once in those wells, and the tips are changed.
8. The solution (20 μl each) is taken from the wells in which dilution is performed immediately before, and moved to the wells of the next row.
9. Pipetting is performed once, and tips are changed.
10. The operations of 8 and 9 are repeated to the 11th row.
11. The flat plate on which the NCI-H1299 cells are inoculated is taken out from an incubator.
12. The virus solution is taken in a volume of 50 μl each from the wells of round plate, and added to the NCI-H1299 cells in the wells of the flat plate by using an 8-tip pipetter starting from the wells of the 12th row of the lowest concentration.
13. The cells were incubated at 37° C. for 120 hours (5 days) in 5% $CO_2$.
14. Wells in which 50% CPE is observed are counted. The titer is calculated in accordance with the following equation.

$$\text{Log}_{10}(\text{TCID}_{50})=L+d(S-0.5)+\log_{10}(1/v)$$

[In Vivo Test (Anticancer Effect, Biochemical Inspection, H&E Staining)]
(Materials and Reagents)
150-mm Dish
NCI-H1299 cells ($5\times10^6$ cells/100 μl PBS/mouse) (04/01 Thawing T175 2 passage)
RPMI 1640 w/10% FBS (growth medium)
PBS
18G Needle (Invitrogen Cat#11668-019, Lot#890730)
27G Needle
1 ml TERUMO syringe
Virus
CVB3-WT ($2.66\times10^9$ $TCID_{50}$/ml, about 1.88 μl/mouse)
CVB3-miR-1&217T ($3.55\times10^8$ $TCID_{50}$/ml, about 14.1 μl/mouse)
CVB3-miR-217T ($2.66\times10^8$ $TCID_{50}$/ml, about 19 μl/mouse)
1 ml TERUMO syringe (29G)
Opti-MEM (registered trademark) I
(Methods)
1. The NCI-H2199 cells are inoculated on 16 of 150-mm dishes.
2. The cells of 4 dishes are removed and collected into 50-ml tubes. The 50-ml tubes in a number of 4 in total are subjected to centrifugation (4° C., 1,000 rpm, 5 minutes).
3. The pellets of two of the tubes are suspended in PBS (20 ml). These are mixed to prepare a suspension of a total volume of 40 ml.

4. The suspension was centrifuged at 1,000 rpm for 5 minutes at 4° C.
5. The NCI-H1299 cells are re-suspended in PBS at $5\times10^7$ cells/ml.
6. The aforementioned suspension (100 μl) is subcutaneously injected to the right abdominal part of BALB/c nu/nu.
7. After 2 days, each virus diluted to $5\times10^6$ $TCID_{50}$/50 μl with Opti-MEM is intratumorally administered.
8. The aforementioned virus administration is performed every other day 5 times in total.
9. Diameters of tumor (major axis and minor axis), and body weight are measured every other day.

Alternatively, the following operations are performed instead of the operations of 8 and 9 mentioned above.

8. After further 2 days, blood and organs are extracted from the mouse.
9. The blood is centrifuged, and the supernatant is used for biochemical tests. The organs are fixed with PFA, then dehydrated, and stained with H&E.

II. Improvement in Aggressiveness by Insertion of GM-CSF

The inventors of the present invention attempted to prepare a genetically modified virus inserted with the granulocyte-macrophage colony-stimulating factor (GM-CSF) for the purpose of further increasing the tumor regression effect for cases where radical cure of tumor was not obtained with the wild-type CVB3 (CVB-WT).

II-1. Results

The inventors of the present invention examined the conditions of the genetic modification with paying attention to the following three points. The first one is the isolation method of mGM-CSF ($3C^{pro}$, $2A^{pro}$, IRES, 2A peptide). The second one is the insertion site of the gene (directly downstream from the initiation point ATG, upstream from the 2A gene, or 3' UTR of the genome of CVB3-WT). The third one is the difference in the protease recognition sequence (comparison with sequences derived from other viruses). A table summarizing the examination results is shown below.

[Use of $3C^{pro}$ and Insertion of mGM-CSF Immediately Downstream from ATG ($1^{st}$ Generation and $2^{nd}$ Generation)]

First, by using $3C^{pro}$, of which use for genetic modification of viruses of the genus *Enterovirus* had been reported, the insertion was performed immediately downstream from ATG. As a result, the cytopathogenic effect (CPE) was not observed for CVB3 inserted with the mGM-CSF gene. However, for the EGFP-inserted CVB3 (CVB3-EGFP) that was prepared as a control and could be confirmed, expression of EGFP was confirmed as previously reported, and CPE could be observed (FIG. 10). This result suggested a possibility that insertion of mGM-CSF immediately downstream from ATG by using $3C^{pro}$ is inappropriate. In addition, insertion into 3' UTR (upstream or downstream from the stop codon) using IRES or 2A peptide was also attempted as the $3^{rd}$ generation and $4^{th}$ generation, but the same results were obtained.

[Use of $2A^{pro}$ and Insertion of mGM-CSF Immediately Upstream from 2A Gene ($5^{th}$ Generation and $6^{th}$ Generation)]

In consideration of the above results, it was examined which protein isolation method among $3C^{pro}$, $2A^{pro}$, IRES, and 2A peptide could derive CPE and isolate mGM-CSF. As a result, CVB3 inserted with mGM-CSF immediately upstream from the 2A gene by using $2A^{pro}$ induced CPE, and expression of mGM-CSF was confirmed by ELISA. Furthermore, when $2A^{pro}$ recognition sequence inserted simultaneously with mGM-CSF was examined, it was found that CPE was more strongly induced with the $2A^{pro}$ recognition sequence derived from poliovirus compared with $2A^{pro}$ recognition sequence derived from CVB3 (FIG. 12), and CVB3 of a higher virus titer could be obtained with the $2A^{pro}$ recognition sequence derived from poliovirus. However, even in CVB3 inserted with mGM-CSF immediately upstream from the 2A gene by using $2A^{pro}$, virus titer applicable to an in vivo experiment could not be obtained.

TABLE 3

| | Location | Isolation Method | Gene expression (EGFP can be observed with fluorescence, GM-CSF is evaluated based on detection amount) oo; fairly rapid or high, o; rapid or high, -; slightly detected, x; below detection limit | CPE ooo; fairly rapid (around 6 h), oo; rapid (around 10 h), o; slow (12 h or longer). -; fairly slow (24 h or longer), x; no CPE |
|---|---|---|---|---|
| $1^{st}$ | Downstream from ATG | $3C^{pro}$ | o CVB3-EGFP | x |
| $2^{nd}$ | Downstream from ATG | $3C^{pro}$ | oo CVB3-Cla&Sbf-EGFP<br>- CVB3-Cla&Sbf-GM-CSF | ooo CVB3-Cla&Sbf-EGFP<br>x CVB3-Cla&Sbf-GM-CSF |
| $3^{rd}$ | Downstream from stop codon | IRES | o CVB3-IRES-EGFP<br>o CVB3-IRES-GM-CSF | - CVB3-IRES-EGFP<br>- CVB3-IRES-GM-CSF |
| $4^{th}$ | Upstream from stop codon | 2A peptide | x CVB3-2A-EGFP<br>x CVB3-2A-GM-CSF | x CVB3-2A-EGFP<br>x CVB3-2A-GM-CSF |
| $5^{th}$ | Upstream from 2A protease | $2A^{pro}$ | o CVB3-G-EGFP-T<br>x CVB3-TG-EGFP-TG<br>o CVB3-GAFGQQ-EGFP-MTNT<br>x CVB3-G-GM-CSF-T<br>x CVB3-TG-GM-CSF-TG<br>o CVB3-GAFGQQ-GM-CSF-MTNT | o CVB3-G-EGFP-T<br>x CVB3-TG-EGFP-TG<br>o CVB3-GAFGQQ-EGFP-MTNT<br>x CVB3-G-GM-CSF-T<br>x CVB3-TG-GM-CSF-TG<br>o CVB3-GAFGQQ-GM-CSF-MTNT |
| $6^{th}$ | Upstream from 2A protease | $2A^{pro}$ (GQQ deletion (LTTY substitution) | x CVB3-GAF-EGFP-MTNT<br>oo CVB3-GAFGQQ-GM-CSF-LTTY | x CVB3-GAF-EGFP-MTNT<br>oo CVB3-GAFGQQ-GM-CSF-LTTY |
| $7^{th}$ | Downstream from ATG | $3C^{pro}$ | o CVB3-EGFP-ALFQ<br>oo CVB3-EGFP-AVFQ<br>x CVB3-GM-CSF-ALFQ<br>o CVB3-GM-CSF-AVFQ | o CVB3-EGFP-ALFQ<br>oo CVB3-EGFP-AVFQ<br>x CVB3-GM-CSF-ALFQ<br>o CVB3-GM-CSF-AVFQ |
| $8^{th}$ | Downstream from ATG | 2A peptide<br>$2A^{pro}$<br>$3C^{pro}$ | o CVB3-GM-CSF-2A (2A peptide)<br>o CVB3-GM-CSF-LTTY ($2A^{pro}$)<br>o CVB3-GM-CSF-AVFQ ($3C^{pro}$) | - CVB3-GM-CSF-2A (2A peptide)<br>ooo CVB3-GM-CSF-LTTY ($2A^{pro}$)<br>oo CVB3-GM-CSF-AVFQ ($3C^{pro}$) |

[Use of $2A^{pro}$ and Insertion of mGM-CSF Immediately Downstream from ATG ($8^{th}$ Generation)]

In consideration of the above results, attention was paid again to the position immediately downstream from ATG, which was the insertion position of CVB3-EGFP providing high virus titer usable for in vivo experiment. CVB3-mGM-CSF was prepared, in which the insertion was performed immediately downstream from ATG by using $2A^{pro}$. CVB3-mGM-CSF showing a high titer usable for the in vivo experiment could be obtained. Sufficient virus titer could not be expected with use of poliovirus-derived sequence and $3C^{pro}$ as well as insertion of mGM-CSF immediately downstream from ATG ($7^{th}$ generation).

[In Vivo Test of CVB3-GM-CSF]

In vivo antitumor effect of genetically modified CVB3-GM-CSF (inserted sequence was the aforementioned $8^{th}$ generation CVB3-GM-CSF-LTTY, the polynucleotide of SEQ ID NO: 4). Tumor (mouse lung cancer, TC-1 cells) was inoculated in the right abdominal parts of C57BL/6 mice on the day 0, and CVB3-WT or CVB3-GM-CSF was intratumorally administered every other day from the day 4 twice in total ($5\times10^6$ $TCID_{50}$/time). As a result, the genetically modified CVB3-GM-CSF exhibited oncolytic property higher than that of WT.

[Subsummary]

According to the present invention, mGM-CSF was inserted into the genome of *Enterovirus* virus for the first time, and mGM-CSF was expressed and isolated by methods completely different from those previously reported. The idea of expressing a foreign protein with maintaining the cytopathogenic effect of enterovirus is extremely heretical for enteroviruses of which pathogenicity have been studied, and it is considered that the originality and novelty of the present invention are extremely high.

II-2. Methods Summary

This research was done according to the following protocols.

[Experiment of $5^{th}$ Generation]

<1st Double Joint PCR>

(Materials and Reagents)

CVB3-WT Plasmid (1) (approx. 10 ng/μl)
pMXs-eGFP (approx. 100 ng/μl) or
KOD -Plus- Neo (TOYOBO Cat KOD-401)
UltraPure
Primers (15 pmol/μl)

TABLE 4

| Name | Sequence |
|---|---|
| CVB3-Forward | GCACTCACTGCTGCTGAGAC (SEQ ID NO: 11) |
| CVB3-Reverse | AGGTCATCGTGGTTCCTCAC (SEQ ID NO: 12) |
| EGFP-Forward | Gtgagcaagggcgaggagct (SEQ ID NO: 13) |
| EGFP-Reverse | Cttgtacagctcgtccatgc (SEQ ID NO: 14) |
| CVB3-G-EGFP-T-Fw | AtcactctcggcatggacgagctgtacaagACGggcgcatttggacaacaatcaggggcagTg (SEQ ID NO: 15) |
| CVB3-G-EGFP-T-Rev | CccggtgaacagctcctcgcccttgctcacGCCcgtatttgtcattgtagtgatgctttgcct (SEQ ID NO: 16) |
| CVB3-TG-EGFP-TG-Fw | AtcactctcggcatggacgagctgtacaagACGGGCggcgcatttggacaacaatcaggggcagTg (SEQ ID NO: 17) |
| CVB3-TG-EGFP-TG-Rev | CccggtgaacagctcctcgcccttgctcacGCCCGTcgtatttgtcattgtagtgatgctttgcct (SEQ ID NO: 18) |
| GAFGQQ-EGFP-MTNT-Fw | AtcactctcggcatggacgagctgtacaagATGACAAATACGggcgcatttggacaacaatcaggggcagTg (SEQ ID NO: 19) |
| GAFGQQ-EGFP-MTNT-Rev | CccggtgaacagctcctcgcccttgctcacTTGTTGTCCAAATGCGCCcgtatttgtcattgtagtgatgctttgcct (SEQ ID NO: 20) |

(Methods)

1. The components were mixed in the following order in a 0.2-ml PCR tube on ice.

TABLE 5

| Reagent | CVB3-VP1 | CVB3-2A | EGFP |
|---|---|---|---|
| UltraPure | 33 μl | 33 μl | 33 μl |
| 10× Buffer | 5 μl | 5 μl | 5 μl |
| 2 mM dNTPs | 5 μl | 5 μl | 5 μl |
| 25 mM $MgSO_4$ | 3 μl | 3 μl | 3 μl |
| Plasmid | CVB3-WT(1) 1 μl | CVB3-WT(1) 1 μl | pMX-EGFP 1 μl |
| Primer Forward (1 μl) | CVB3-Forward | CVB3-G-EGFP-T-Fw<br>CVB3-TG-EGFP-TG-Fw<br>GAFGQQ-EGFP-MTNT-Fw | EGFP-Forward |
| Primer Reverse (1 μl) | CVB3-G-EGFP-T-Rev<br>CVB3-TG-EGFP-TG-Rev<br>GAFGQQ-EGFP-MTNT-Rev | CVB3-Reverse | EGFP-Reverse |
| KOD -Plus- Neo | 1 μl | 1 μl | 1 μl |

2. The following program is executed by using Mastercycler (registered trademark) Pro (Eppendorf).

94° C. 2:00, 98° C. 0:10, 68° C. 2:00 (10 cycles), 72° C. 7:00

Agarose gel electrophoresis is performed by using three kinds of PCR products, and the target bands are excised. Nucleic acids are extracted from the excised gel.

<2nd Double Joint PCR>

(Materials and Reagents)

1st Joint PCR product (VP1 side:EGFP:2A side=1:3:1, molar ratio)

VP1 product obtained after PCR gel extraction (three kinds of T, TG, and MTNT)

EGFP product obtained after PCR gel extraction 2A product obtained after PCR gel extraction (three kinds of T, TG, and MTNT)

KOD -Plus- Neo (TOYOBO Cat# KOD-401)

(Methods)

1. The components are mixed in the following order in a 0.2-ml PCR tube on ice.

TABLE 6

| Reagent | EGFP |
|---|---|
| UltraPure | 31 μl |
| 10× Buffer | 5 μl |
| 2 mM dNTPs | 5 μl |
| 25 mM $MgSO_4$ | 3 μl |
| VP1 PCR product (1 μl in 30 μl after gel extraction) | 1 μl |
| EGFP PCR product (1 μl in 30 μl after gel extraction) | 3 μl |
| 2A PCR product (1 μl in 30 μl after gel extraction) | 1 μl |
| KOD -Plus- Neo | 1 μl |

2. The following program is executed by using Mastercycler (registered trademark) Pro (Eppendorf).

94° C. 2:00, 98° C. 0:10, 68° C. 4:00 (15 cycles), 72° C. 7:00

<3rd Double Joint PCR>

(Materials and Reagents)

2nd Joint PCR product (three kinds of T, TG, and MTNT)

KOD -Plus- Neo (TOYOBO Cat# KOD-401)

Primers (15 pmol/μl)

TABLE 7

| Name | Sequence |
|---|---|
| CVB3-Forward | GCACTCACTGCTGCTGAGAC (SEQ ID NO: 21) |
| CVB3-Reverse | AGGTCATCGTGGTTCCTCAC (SEQ ID NO: 22) |

(Methods)

1. The components are mixed in the following order in a 0.2-ml PCR tube on ice.

TABLE 8

| Reagent | One among 3 kinds of T, TG, and MTNT |
|---|---|
| UltraPure | 33 μl |
| 10× Buffer | 5 μl |
| 2 mM dNTPs | 5 μl |
| 25 mM $MgSO_4$ | 3 μl |
| 2nd joint PCR product | 1 μl |
| Primer Forward | 1 μl |
| Primer Reverse | 1 μl |
| KOD -Plus- | 1 μl |

2. The following program is executed by using Mastercycler (registered trademark) Pro (Eppendorf).

94° C. 2:00, 98° C. 0:10, 68° C. 2:00 (35 cycles), 72° C. 7:00

3. The double joint PCR product was purified, and the product and the CVB3 plasmid are treated with restriction enzymes EcoRI and SpeI.

4. Agarose gel electrophoresis is performed by using the restriction enzyme treatment products, and the target bands are excised.

5. After the gel purification, the CVB3 plasmid treated with the restriction enzymes and the overlap extension PCR product treated with the restriction enzymes are reacted at 16° C. for 2 hours by using Ligation High.

6. The ligation product is introduced into competent cells, and the cells are cultured at 37° C.

7. Colonies are picked up on the next day, and cultured in LB medium.

8. Plasmids are collected from the culture, and insertion of the target sequence is confirmed.

<From Preparation of Virus RNA to Measurement of Virus Titer>

Since the following procedures are the same as the protocols for CVB3-miRT, they are omitted.

[Experiment of $6^{th}$ Generation]

<Mutagenesis>

(Materials and Reagents)

CVB3-MTNT-Plasmid (1) (approx. 10 ng/μl)

pMXs-eGFP (approx. 100 ng/μl) or

KOD -Plus- Neo (TOYOBO Cat# KOD-401)

UltraPure

Primers (15 pmol/μl)

```
LTTY substitution Forward
                                    (SEQ ID NO: 23)
CTTACAACGTACggcgcatttggacaacaatcag

GQQ deletion Forward
                                    (SEQ ID NO: 24)
AAATGCCGCCcgtatttgtca
```

(Methods)

1. The components are mixed in the following order in a 0.2-ml PCR tube on ice.

TABLE 9

| Reagent | CVB3-LTTY-GAFGQQ | CVB3-MTNT-GAF |
|---|---|---|
| UltraPure | 33 μl | 33 μl |
| 10× Buffer | 5 μl | 5 μl |
| 2 mM dNTPs | 5 μl | 5 μl |
| 25 mM $MgSO_4$ | 3 μl | 3 μl |
| Plasmid | 1 μl | 1 μl |
| Primer Forward | CVB3-miR-Forward | Arbitrary miRT-Forward |
| Primer Reverse | Arbitrary miRT-Reverse | CVB3-miR-Reverse |
| KOD -Plus- Neo | 1 μl | 1 μl |

2. The following program is executed by using Mastercycler (registered trademark) Pro (Eppendorf).

94° C. 2:00, 98° C. 0:10, 68° C. 12:00 (15 cycles), 72° C. 7:00

<DpnI Digestion>

(Materials and Reagents)

Inverse PCR product

DpnI (10 U/μl, NEB, Cat# R0176S)

Ligation High (TOYOBO, Cat# LGK-101)

T4 Polynucleotide Kinase (5 U/μl, TOYOBO, Cat# PNK-111)
UltraPure
(Methods)
1. DpnI (2 μl) is added to the whole volume (50 μl) of the inverse PCR product, and sufficiently stirred by pipetting.
2. The reaction is allowed at 37° C. for 2 hours.
3. The following components are added to a new PCR tube in the following order to prepare a reaction mixture.

TABLE 10

| Reagent | Volume |
| --- | --- |
| PCR product treated with DpnI | 2 μl |
| UltraPure | 7 μl |
| Ligation High | 5 μl |
| T4 Polynucleotide Kinase (5 U/μl) | 1 μl |
| Total | 15 μl |

4. The reaction is allowed at 16° C. for 1 hour.
5. A part of the reaction mixture (up to 10 μl) is used to transform *Eschericia coli*, and culture is performed at 37° C.
6. Colonies are picked up on the next day, and cultured in LB medium.
7. Plasmids are collected from the culture, and presence or absence of mutation is confirmed.
<From Preparation of Virus RNA to Measurement of Virus Titer>
Since the following procedures are the same as the protocols for CVB3-miRT, they are omitted.
[Experiment of 8$^{th}$ Generation]
<Construction of Vector>
(Materials and Reagents)
 CVB3-WT Plasmid (approx. 10 ng/μl)
 pMXs-eGFP (approx. 100 ng/μl) or pORF9-mGMCSF (approx. 100 ng/μl)
 KOD -Plus- Neo (TOYOBO, Cat KOD-401)
 UltraPure
 Primers (15 pmol/μl)

TABLE 11

| | Restriction enzyme sequence (ClaI & SbfI-inserted CVB3) | |
| --- | --- | --- |
| | Name | Sequence |
| (1) | CVB3-Forward | tataccccctcccccaactg (SEQ ID NO: 25) |
| (2) | CVB3-Reverse | Agcaagcatccttggtggaa (SEQ ID NO: 26) |
| (3) | Cla&Sbf-Forward | atggcagctcaaatcgattt tgggggccctgcagggagg ctttgtttcaaggagctcaa gtatcaacgcaa (SEQ ID NO: 27) |
| (4) | Cla&Sbf-Reverse | tccttgaaacaaagcctccc tgcagggccccccaaaatcg atttgagctgccattttgct gtattcaactta (SEQ ID NO: 28) |
| (5) | Cla-EGFP-Forward | GGGCCCAAAATCGATgtgag caagggcgaggagct (SEQ ID NO: 29) |

TABLE 11-continued

| | Restriction enzyme sequence (ClaI & SbfI-inserted CVB3) | |
| --- | --- | --- |
| | Name | Sequence |
| (6) | Sbf-EGFP-Reverse | GGGCCCAAACCTGCAGGGct tgtacagctcgtccatgc (SEQ ID NO: 30) |
| (7) | Cla-mGMCSF-Forward | GGGCCCAAAATCGATtggct gcagaatttactttt (SEQ ID NO: 31) |
| (8) | Sbf-mGMCSF-Reverse | GGGCCCAAACCTGCAGGGtt tttggcctggttttttgc (SEQ ID NO: 32) |

TABLE 12

| | Restriction enzyme sequence (SfiI-inserted CVB3) | |
| --- | --- | --- |
| | Name | Sequence |
| (1) | CVB3-Forward | Tataccccctcccccaactg (SEQ ID NO: 33) |
| (2) | CVB3-Reverse | Agcaagcatccttggtggaa (SEQ ID NO: 34) |
| (3) | Sfi-AVFQ-Forward | GGGGCCGGAGGGGCCggact tagacaagcagttttcaag gagctcaagtatcaacgcaa aag (SEQ ID NO: 35) |
| (4) | Sfi-AVFQ-Reverse | ttgaaaaactgcttgtctaa gtccGGCCCCTCCGGCCCCc attttgctgtattcaactta acaatg (SEQ ID NO: 36) |
| (5) | Sfi-EGFP-Forward | aaaaaaGGCTGAGAGGCCg tgagcaagggcgaggagctg (SEQ ID NO: 37) |
| (6) | Sfi-EGFP-Reverse | aaaaaaGGCCTCTCTGGCct tgtacagctcgtccatgc (SEQ ID NO: 38) |
| (7) | Sfi-mGMCSF-Forward | aaaaaaGGCCTGAGAGGCCt ggctgcagaatttactttc ctg (SEQ ID NO: 39) |
| (8) | Sfi-mGMCSF-Reverse | aaaaaaGGCCTCTCTGGCct tttggcctggtttttg (SEQ ID NO: 40) |

CVB3 inserted with the aforementioned 2 kinds (each table) of sequences for restriction enzyme is produced, and the sequence of EGFP or mGM-CSF is inserted by using the inserted restriction enzyme sequence. The following is a protocol common to the two kinds. The same operations are performed according to the primer number.
(Methods)
1. The components are mixed in the following order in a 0.2-ml PCR tube on ice.

TABLE 13

| Reagent | First-half | Second half |
| --- | --- | --- |
| UltraPure | 33 μl | 33 μl |
| 10× Buffer for KOD-Plus- | 5 μl | 5 μl |
| 2 mM dNTPs | 5 μl | 5 μl |
| 25 mM MgSO$_4$ | 3 μl | 3 μl |

TABLE 13-continued

| Reagent | First-half | Second half |
| --- | --- | --- |
| Plasmid | 1 µl | 1 µl |
| Primer Forward | (1) | (3) |
| Primer Reverse | (4) | (2) |
| KOD -Plus- Neo | 1 µl | 1 µl |

2. The mixture is stirred by tapping or gentle pipetting, and gently spun down, and the solution is collected.
3. The following program is executed with a thermal cycler (Bio-Rad).
94° C. 2:00, 98° C. 0:10, 62° C. 0:15, 68° C. 1:30 (20 cycles), 72° C. 7:00
4. Overlap extension PCR is performed by using the two PCR products.
5. These two PCR products are each put into a tube in a volume of 1 µl, and used as the template together with the CVB3-miR-Forward and CVB3-miR-Reverse primers to perform PCR. The aforementioned program is executed for 30 cycles.
6. The overlap extension PCR product is purified, and the product and the CVB3 plasmid are treated with the restriction enzymes BlpI and XmaI.
7. Agarose gel electrophoresis is performed with the product obtained after the restriction enzyme treatment, and target bands are excised.
8. After the gel purification, the CVB3 plasmid treated with the restriction enzymes and the overlap extension PCR product treated with the restriction enzymes are reacted at 16° C. for 2 hours by using Ligation High.
9. The ligation product is introduced into competent cells, and the cells are cultured at 37° C.
10. Colonies are picked up on the next day, and cultured in LB medium.
11. Plasmids are collected from the culture, and insertion of the restriction enzyme sequence is confirmed.
<Insert PCR>
(Methods)
1. The following components are mixed in the following order in a 0.2-ml PCR tube on ice.

TABLE 14

| Reagent | EGFP | mgM-CSF |
|---|---|---|
| UltraPure | 33 μl | 33 μl |
| 10× Buffer | 5 μl | 5 μl |
| 2 mM dNTPs | 5 μl | 5 μl |
| 25 mM $MgSO_4$ | 3 μl | 3 μl |
| pMXs-eGFP or pORF9-mGMCSF (1 μl) | pMXs-eGFP | pORF9-mGMCSF |
| Primer-Forward (1 μl) | (5) | (7) |
| Primer-Reverse (1 μl ) | (6) | (8) |
| KOD -Plus- Neo | 1 μl | 1 μl |

2. The following program is executed by using Mastercycler (registered trademark) Pro (Eppendorf).
94° C. 2:00, 98° C. 0:15, 68° C. 1:30 (35 cycles), 72° C. 7:00
3. The PCR product is purified, and the product and the restriction enzyme sequence-inserted CVB3 plasmid are treated with restriction enzymes ClaI and SbfI or SfiI.
4. Agarose gel electrophoresis is performed by using the restriction enzyme treatment product, and the target bands are excised.
5. After the gel purification, the CVB3 plasmid treated with the restriction enzymes and the PCR product treated with the restriction enzymes are reacted at 16° C. for 2 hours by using Ligation High.
6. The ligation product is introduced into competent cells, and the cells are cultured at 37° C.
7. Colonies are picked up on the next day, and cultured in LB medium.
8. Plasmids are collected from the culture, and insertion of EGFP or mGMCSF sequence is confirmed.
<Mutagenesis PCR>
(Materials and Reagents)
CVB3-MTNT-Plasmid (1) (approx. 10 ng/μl)
pMXs-eGFP (approx. 100 ng/μl) or
KOD -Plus- Neo (TOYOBO, Cat# KOD-401)
UltraPure
Primers (15 pmol/μl)

TABLE 15

| Name | Sequence |
|---|---|
| Inverse-2A-peptide-Fw | GAGGGCAGAGGAAGTCTTCTAA CATGCGGTGACGTGGAGGAGAA TCCCGGCCTggagctcaagtat caacgcaaaagactgggg (SEQ ID NO: 41) |
| DLTTY-Fw | CCCTGCAGGGATCTTACAACGT ACGGAGCTCAAGTATCAACGCA Aaagactgggg (SEQ ID NO: 42) |
| CCEPAGLRQAVFQ-Fw | GCCAGAGGGGCCTGCTGCGAGT TTGCAggacttagacaagcagt tttcaa (SEQ ID NO: 43) |
| Inverse-GMCSF-Rev | tttttggcctggttttttgcat tcaaagggg (SEQ ID NO: 44) |

(Methods)
1. The components are mixed in the following order in a 0.2-ml PCR tube on ice.

TABLE 16

| Reagent | CVB3-2A peptide | CVB3-$2A^{pro}$ | CVB3-$3C^{pro}$ |
|---|---|---|---|
| UltraPure | 33 μl | 33 μl | 33 μl |
| 10× Buffer | 5 μl | 5 μl | 5 μl |
| 2 mM dNTPs | 5 μl | 5 μl | 5 μl |
| 25 mM $MgSO_4$ | 3 μl | 3 μl | 3 μl |
| Plasmid (1 μl) | CVB3-Cla&Sbf-mGM-CSF | CVB3-Cla&Sbf-mGM | CVB3-Sfi-mGM-CSF |
| Primer-Forward (1 μl) | Inverse-2A-peptide-Fw | DLTTY-Fw | CCEFAGLRQAVFQ-Fw |
| Primer-Reverse (1 μl ) | Inverse-GMCSF-Rev | Inverse-GMCSF-Rev | Inverse-GMCSF-Rev |
| KOD -Plus- Neo | 1 μl | 1 μl | 1 μl |

2. The following program is executed by using Mastercycler (registered trademark) Pro (Eppendorf).

94° C. 2:00, 98° C. 0:10, 68° C. 12:00 (15 cycles), 72° C. 7:00

<DpnI Digestion>

(Materials and Reagents)

Inverse PCR product

DpnI (10 U/μl, NEB, Cat# R0176S)

Ligation High (TOYOBO, Cat# LGK-101)

T4 Polynucleotide kinase (5 U/μl, TOYOBO, Cat# PNK-111)

UltraPure (Methods)

1. DpnI (2 μl) is added to the whole volume (50 μl) of the inverse PCR product, and sufficiently stirred by pipetting.
2. The reaction is allowed at 37° C. for 2 hours.
3. The following components are added to a new PCR tube in the following order to prepare a reaction mixture.

TABLE 17

| Reagent | Volume |
|---|---|
| PCR product treated with DpnI | 2 μl |
| UltraPure | 7 μl |
| Ligation High | 5 μl |
| T4 Polynucleotide Kinase (5 U/μl) | 1 μl |
| Total | 15 μl |

4. The reaction is allowed at 16° C. for 1 hour.
5. A part of the reaction mixture (up to 10 μl) is used to transform *Eschericia coli*, and culture is performed at 37° C.
6. Colonies are picked up on the next day, and cultured in LB medium.
7. Plasmids are collected from the culture, and presence or absence of mutation is confirmed.

<From Preparation of Virus RNA to Measurement of Virus Titer>

Since the following procedures are the same as the protocols for CVB3-miRT, they are omitted.

[ELISA] (mGM-CSF, R&D)

(Materials and Reagents)

Mouse GM-CSF Immunoassay (R&D Systems, Cat# PMGM00)

Milli-Q (600 ml, autoclaved)

Cell supernatant

CVB3-mGMCSF-infected NCI-H1299 cells (Methods)

1. About 600 ml of Milli-Q is sterilized by autoclaving.
2. Wash buffer concentrate (25×, 25 ml) is added to cooled Milli-Q, and thereby diluted to a total volume of 625 ml (1×).
3. The attached microplate strips in a required number are set on a plate frame. Those not used are returned into the foil.
4. Assay Diluent RD1W is add to each well in a volume of 50 μl.
5. Standard solutions were successively added to the wells (Assay Diluent is already added) in a volume of 50 μl each from the solution of the lowest concentration in the ascending order of the concentration. The sample (50 μl) is added to each well (Assay Diluent is already added) in a similar manner, and the frame is gently tapped for 1 minute.
6. The plate was firmly sealed with a cover seal, and left standing at room temperature for 2 hours.
7. The liquid in each well is sucked, and 400 μl of the wash buffer (prepared in 2 mentioned above) is added to each well.
8. The operation of 7 mentioned above is repeated 5 times in total. Finally, moisture is swiped with clean Kim Towel.
9. Mouse GM-CSF conjugate (100 μl) is added to each well.
10. A new cover seal is stuck, and the plate was left standing at room temperature for 2 hours.
11. The aforementioned washing operation is repeated.
12. A substrate solution (100 μl) is added to each well.
13. The plate is left standing at room temperature for 30 minutes in a dark place without the seal.
14. A stop solution (100 μl) is added to each well.
15. The plate is gently tapped until the regents are mixed.
16. Absorbance is measured at 450 nm within 30 minutes by using a plate reader.

[In Vivo Test]

(Materials and Reagents)

150-mm Dish

TC-1 cells ($1\times10^6$ cells/100 μl PBS/mouse) (03/20 Thawing T175 2 passage)

RPMI 1640 w/10% FBS, 1 mM sodium pyruvate (growth medium)

PBS

18G Needle

27G Needle 1 ml TERUMO syringe

Virus

CVB3-WT ($3.33\times10^8$ $TCID_{50}$/ml, about 15 μl/mouse)

CVB3-mGM-CSF ($1.12\times10^8$ $TCID_{50}$/ml, about 45 μl/mouse)

1 ml TERUMO syringe (29G)

Opti-MEM (registered trademark) I (Methods)

1. The TC-1 cells are inoculated on 150-mm dishes.
2. The cells of 4 dishes are removed and collected in 50-ml tubes. In total, 4 of the 50-ml tubes are subjected to centrifugation (4° C., 1,000 rpm, 5 minutes).
3. The pellets of two of the tubes are suspended in PBS (20 ml). These are mixed to prepare a suspension of a total volume of 40 ml.
4. The suspension was centrifuged at 1,000 rpm for 5 minutes at 4° C.
5. The TC-1 cells are re-suspended in PBS at $1\times10^7$ cells/ml.
6. The aforementioned suspension (100 μl) is subcutaneously injected to the right abdominal part of C57BL/6.
7. After 4 days, each virus diluted to $5\times10^6$ $TCID_{50}$/50 μl with Opti-MEM is intratumorally administered.
8. The aforementioned virus administration is performed every other day 2 times in total.
9. Diameters of tumor (major axis and minor axis), and body weight are measured every other day.

SEQUENCE LISTING FREE TEXT

SEQ ID NO: 1, miR-1 & 217T (×2)
SEQ ID NO: 2, miR-217 (×4)
SEQ ID NO: 3, CVB3-GM-CSF-2A
SEQ ID NO: 4, CVB3-GM-CSF-LTTY
SEQ ID NO: 5, CVB3-GM-CSF-AVFQ
SEQ ID NO: 6, CVB3-miR-Forward primer
SEQ ID NO: 7, CVB3-miR-Reverse primer
SEQ ID NO: 8, miR-1&217T Forward primer
SEQ ID NO: 9, miR-1&217T Reverse primer
SEQ ID NO: 10, miR-217T Forward primer
SEQ ID NO: 11, CVB3-Forward primer
SEQ ID NO: 12, CVB3-Reverse primer
SEQ ID NO: 13, EGFP-Forward primer
SEQ ID NO: 14, EGFP-Forward primer
SEQ ID NO: 15, CVB3-G-EGFP-T-Fw primer SEQ ID NO: 16, CVB3-G-EGFP-T-Rev primer
SEQ ID NO: 17, CVB3-TG-EGFP-TG-Fw primer
SEQ ID NO: 18, CVB3-TG-EGFP-TG-Rev primer
SEQ ID NO: 19, GAFGQQ-EGFP-MTNT-Fw primer
SEQ ID NO: 20, GAFGQQ-EGFP-MTNT-Rev primer
SEQ ID NO: 21, CVB3-Forward primer
SEQ ID NO: 22, CVB3-Reverse primer
SEQ ID NO: 23, LTTY substitution Forward primer
SEQ ID NO: 24, GQQ deletion Forward primer
SEQ ID NO: 25, CVB3-Forward primer
SEQ ID NO: 26, CVB3-Reverse primer
SEQ ID NO: 27, Cla&Sbf-Forward primer
SEQ ID NO: 28, Cla&Sbf-Reverse primer
SEQ ID NO: 29, Cla-EGFP-Forward primer
SEQ ID NO: 30, Cla-mGMCSF-Forward primer
SEQ ID NO: 31, CVB3-Forward primer
SEQ ID NO: 32, CVB3-Reverse primer
SEQ ID NO: 33, CVB3-Forward primer
SEQ ID NO: 34, CVB3-Reverse primer
SEQ ID NO: 35, Sfi-AVFQ-Forward primer
SEQ ID NO: 36, Sfi-AVFQ-Reverse primer
SEQ ID NO: 37, Sfi-EGFP-Forward primer
SEQ ID NO: 38, Sfi-EGFP-Reverse primer
SEQ ID NO: 39, Sfi-mGMCSF-Forward primer
SEQ ID NO: 40, Sfi-mGMCSF-Reverse primer
SEQ ID NO: 41, Inverse-2A-peptide-Fw primer
SEQ ID NO: 42, DLTTY-Fw primer
SEQ ID NO: 43, CCEFAGLRQAVFQ-Fw primer
SEQ ID NO: 44, Inverse-GMCSF-Rev primer

The invention claimed is:

1. A modified coxsackievirus of which proliferation is suppressed in a tissue-specific manner, which comprises a mutated genome corresponding to genome of coxsackievirus B3 wild-type (CVB3-WT) inserted with at least one polynucleotide consisting of a target sequence of a tissue-specific microRNA (miRNA), wherein the inserted polynucleotide is the polynucleotide of the following sequence of (a) or (b):

```
(a)
ATA CAT ACT TCT TTA CAT TCC Acg atA TAC ATA
CTT CTT TAC ATT CCA acc ggt TCC AAT CAG TTC
CTG ATG CAG TAt cac TCC AAT CAG TTC CTG ATG
CAG TA which is SEQ ID NO: 1; or

(b)
TCC AAT CAG TTC CTG ATG CAG TAc gat TCC AAT
CAG TTC CTG ATG CAG TAa ccg gtT CCA ATC AGT
TCC TGA TGC AGT Atc acT CCA ATC AGT TCC TGA
TGC AGT A which is SEQ ID NO: 2.
```

2. The modified coxsackievirus according to claim 1, wherein the insertion position is in the 3' UTR region of the CVB3-WT genome.

3. The modified coxsackievirus according to claim 1, wherein the insertion position is a position upstream from the position 7344 or downstream from the position between the positions 7304 and 7305 of the CVB3-WT genome.

4. The modified coxsackievirus according to claim 1, wherein the tissue-specific miRNA is one expressed in pancreas and/or myocardium.

5. The modified coxsackievirus according to claim 1, wherein the tissue-specific miRNA consists of miR-1 and/or miR-217.

6. The modified coxsackievirus according to claim 1, wherein 2 to 6 of the polynucleotides consisting of the target sequence are inserted.

7. The modified coxsackievirus according to claim 1, wherein a region encoding granulocyte-macrophage colony-stimulating factor (GM-CSF) is further inserted in an expressible form into the mutated genome.

8. The modified coxsackievirus according to claim 1, wherein a polynucleotide containing a region encoding GM-CSF and a region encoding a 2A protease recognition sequence ligated downstream is further functionally inserted into the mutated genome at a position downstream from ATG of the translation initiation point and upstream from VP4 region.

9. The modified coxsackievirus according to claim 8, wherein the 2A protease recognition sequence is a sequence modified so as to be recognizable by 2A protease derived from poliovirus.

10. The modified coxsackievirus according to claim 1, which has a mutated genome comprising CVB3-WT genome inserted with a region encoding GM-CSF in an expressible form.

11. The modified coxsackievirus according to claim 1, which has a mutated genome comprising CVB3-WT genome functionally inserted with a polynucleotide containing a region encoding GM-CSF and a region encoding a 2A protease recognition sequence ligated downstream at a position downstream from ATG of the translation initiation point and upstream from VP4 region.

12. The modified coxsackievirus according to claim 11, wherein the 2A protease recognition sequence is a sequence modified so as to be recognizable by 2A protease derived from poliovirus.

13. A pharmaceutical composition containing the modified coxsackievirus according to claim 1.

14. The pharmaceutical composition according to claim 13, which is for prophylactic or therapeutic treatment of a lung cancer or a precancerous state thereof.

15. The modified coxsackievirus according to claim 1 for use in a prophylactic or therapeutic treatment of a lung cancer or a precancerous state thereof.

16. A method for a treatment of a lung cancer or a precancerous state thereof: the method comprising administering the modified coxsackievirus according to claim 1 to a subject in need of treating the lung cancer.

17. The pharmaceutical composition according to claim 13, which is a preparation for topical application or systemic administration.

* * * * *